(12) United States Patent
Kumar et al.

(10) Patent No.: US 10,030,246 B2
(45) Date of Patent: Jul. 24, 2018

(54) MAIZE UBIQUITIN PROMOTERS

(71) Applicant: Dow AgroSciences LLC, Indianapolis, IN (US)

(72) Inventors: Sandeep Kumar, Carmel, IN (US); Manju Gupta, Carmel, IN (US); Terry R. Wright, Carmel, IN (US); Susan M. Jayne, Zionsville, IN (US); Doug A. Smith, Noblesville, IN (US); Diaa Alabed, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 168 days.

(21) Appl. No.: 14/587,735

(22) Filed: Dec. 31, 2014

(65) Prior Publication Data
US 2015/0184175 A1 Jul. 2, 2015

Related U.S. Application Data

(60) Provisional application No. 61/922,522, filed on Dec. 31, 2013.

(51) Int. Cl.
*C12N 15/82* (2006.01)
*C12N 15/10* (2006.01)

(52) U.S. Cl.
CPC ......... *C12N 15/8216* (2013.01); *C12N 15/10* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. |
| 4,769,061 A | 9/1988 | Comai |
| 4,810,648 A | 3/1989 | Stalker |
| 4,940,835 A | 7/1990 | Shah et al. |
| 4,975,374 A | 12/1990 | Goodman et al. |
| 5,004,863 A | 4/1991 | Umbeck |
| 5,015,580 A | 5/1991 | Christou et al. |
| 5,159,135 A | 10/1992 | Umbeck |
| 5,266,361 A | 11/1993 | Schwarte et al. |
| 5,302,523 A | 4/1994 | Coffee et al. |
| 5,380,831 A | 1/1995 | Adang et al. |
| 5,384,253 A | 1/1995 | Krzyzek et al. |
| 5,424,276 A | 6/1995 | Cain et al. |
| 5,464,765 A | 11/1995 | Coffee et al. |
| 5,506,195 A | 4/1996 | Ensminger et al. |
| 5,508,184 A | 4/1996 | Negrutiu et al. |
| 5,510,474 A | 4/1996 | Quail et al. |
| 5,538,880 A | 7/1996 | Lundquist et al. |
| 5,550,318 A | 8/1996 | Adams et al. |
| 5,591,616 A | 1/1997 | Hiei et al. |
| 5,607,914 A | 3/1997 | Rao et al. |
| 5,635,055 A | 6/1997 | Sweet et al. |
| 5,659,026 A | 8/1997 | Baszczynski et al. |
| 5,750,871 A | 5/1998 | Moloney et al. |
| 5,767,373 A | 6/1998 | Ward et al. |
| 5,824,877 A | 10/1998 | Hinchee et al. |
| 5,846,797 A | 12/1998 | Strickland |
| 5,981,840 A | 11/1999 | Zhao et al. |
| 6,160,208 A | 12/2000 | Lundquist et al. |
| 6,166,302 A | 12/2000 | Merlo et al. |
| 6,245,968 B1 | 6/2001 | Bouldec et al. |
| 6,268,549 B1 | 7/2001 | Sailland et al. |
| 6,384,301 B1 | 5/2002 | Martinell et al. |
| 6,399,861 B1 | 6/2002 | Anderson et al. |
| 6,403,865 B1 | 6/2002 | Koziel et al. |
| 6,506,559 B1 | 1/2003 | Fire et al. |
| 6,573,099 B2 | 6/2003 | Graham et al. |
| 6,624,344 B1 | 9/2003 | Rangan et al. |
| 6,699,984 B1 | 3/2004 | Ainley et al. |
| 7,060,876 B2 | 7/2006 | Hiei et al. |
| 7,838,733 B2 | 11/2010 | Wright et al. |
| 2003/0066102 A1 | 4/2003 | Maxwell et al. |
| 2003/0135879 A1 | 7/2003 | Weeks et al. |
| 2009/0093366 A1 | 4/2009 | Wright et al. |
| 2009/0104700 A1 | 4/2009 | Samuel et al. |
| 2012/0246763 A1* | 9/2012 | Flasinski .............. C07K 14/415 800/298 |

FOREIGN PATENT DOCUMENTS

| | | |
|---|---|---|
| EP | 0242246 | 10/1987 |
| EP | 0333033 | 9/1989 |
| EP | 418175 | 3/1991 |
| EP | 487352 | 5/1992 |

(Continued)

OTHER PUBLICATIONS

GenBank Accession AY373338. Binary vector pGA1611. Published Nov. 25, 2003. pp. 1-6.*
U.S. Appl. No. 14/587,743, Unpublished.
U.S. Appl. No. 14/587,757, Unpublished.
U.S. Appl. No. 14/587,750, Unpublished.
U.S. Appl. No. 14/587,762, Unpublished.
Loke J., et al., (2005) *Plant Physiology* 138(3); 1457-1468.
Sambrook et al. (ed.), Molecular Cloning: A Laboratory Manual, 2nd ed., vol. 1-3, Cold Spring Harbor Laboratory Press, Cold Spring Harbor, New York, 1989.
Mullis et al., "Specific Enzymatic Amplification of DNA In Vitro: The Polymerase Chain Reaction," *Cold Spring Harbor Symp. Quant. Biol.*, 51:263 (1987).
Erlich, ed., PCR Technology, (Stockton Press, NY, 1989). (Book).
Smith and Waterman (1981) *Adv. Appl. Math.* 2:482.
Needleman and Wunsch (1970) *J. Mol. Biol.* 48:443.
Pearson and Lipman (1988) *Proc. Natl. Acad. Sci. U.S.A.* 85:2444.
Higgins and Sharp (1988) *Gene* 73:237-44.
Higgins and Sharp (1989) *CABIOS* 5:151-3.
Corpet et al. (1988) *Nucleic Acids Res.* 16:10881-90.
Huang etal. (1992) *Comp. Appl. Biosci.* 8:155-65.

(Continued)

*Primary Examiner* — Ashley K Buran
(74) *Attorney, Agent, or Firm* — Marcos P. Rivas; Barnes & Thornburg LLP

(57) ABSTRACT

The Zea mays c.v. B73 Ubiquitin-1 (*Z. mays* c.v. B73 Ubi-1) promoter drives high levels of constitutive transgene expression in plants. Repeated use of the same *Z. mays* c.v. B73 Ubi-1 promoter in multi-gene constructs may also lead to gene silencing, thereby making transgenic products less efficacious. Provided are gene regulatory promoter elements, constructs, and methods for expressing a transgene in plant cells and/or plant tissues using gene regulatory elements from the Ubi-1 promoter of a different *Z. mays* genotype, *Z. mays* c.v. B104.

17 Claims, 10 Drawing Sheets

(56) References Cited

FOREIGN PATENT DOCUMENTS

| EP | 496630 | 7/1992 |
|---|---|---|
| EP | 496631 | 7/1992 |
| EP | 470856 | 12/1992 |
| EP | 560482 | 9/1993 |
| EP | 527036 | 10/1993 |
| EP | 625505 | 11/1994 |
| EP | 625508 | 11/1994 |
| EP | 682659 | 11/1995 |
| WO | 1993/02197 | 4/1993 |
| WO | 1995/06722 | 3/1995 |
| WO | 1997/013402 | 4/1997 |
| WO | 2005/107437 | 11/2005 |
| WO | 2007/053482 | 5/2007 |
| WO | 2009149304 | 12/2009 |
| WO | 2011/146524 | 11/2011 |
| WO | 2013/016546 | 1/2013 |
| WO | 2013101343 | 7/2013 |

OTHER PUBLICATIONS

Pearson et al. "Chapter 26: Using the FASTA Program to Search Protein and DNA Sequence Databaases," *Methods Mol. Biol.* (1994) 24:307-31.
Tatusova and Madden, "BLAST 2 Sequences, a new tool for comparing protein and nucleotide sequences," *FEMS Microbiol. Lett.* (1999) 174:247-50.
Altschul et al. (1990) *J. Mol. Biol.* 215:403-10.
Jennifer, E.F. et al, (2002) *Genes & Dev.*, 16: 2583-2592.
Langridge et al. (1989) Proc. Natl. Acad. Sci. USA 86:3219-23.
Mueller et al. (1978) Cell 15:579-85.
Lewin, *Genes V*, Oxford University Press, 1994; (Book).
Kendrew et al. (eds.), *The Encyclopedia of Molecular Biology*, Blackwell Science Ltd., 1994. (Book).
Meyers (ed.), *Molecular Biology and Biotechnology: A Comprehensive Desk Reference*, VCH Publishers, Inc., 1995. (Book).
Christensen and Quail, 1996, Transenic Research, 5: 213-218.
Christensent et al, 1992, Plant Molecular Biology, 18: 675-689.
Toki et al. "Expression of a Maize Ubiquitin Gene Promoter-bar Chimeric Gene in Transgenic Rice Plants," Plant Physiol. (1992), 100, 1503-1507.
Kumar and Fladung 2002. "Transgene integration in aspen: structures of integration sites and mechanism of T-DNA integration," The Plant Journal, 2002, 31(4), 543-551.
Kumar and Fladung 2000a."Determination of transgene repeat formatio and promoter methylation in transgenic plants," BioTechniques, Jun. 2000, 28:1128-1137.
Kumar and Fladung 2000b., "Transgene repeats in aspen: molecular characterisation sugests simultaneous integration of independent T-DNAs into receptive hotspots in the host genome," Mol Gen Genet (2000), 264: 20-28.
Kumar and Fladung 2001a. "Gene stability in transgenic aspen (Populus). II. Molecular characterization of variable expression of transgene in wild and hybrid aspen," Plants (2001) 213: 731-740.
Kumar and Fladung 2001b., "Controlling transgene integration in plants," Trends in Plant Science, vol. 6, No. 4, Apr. 2001, 155-159.
Mette et al. 1999.
Mourrain et al. "A single transgene locus triggers both transcriptional and post-transcriptional silencing throuh double-sranded RNA production," Planta (2007), 225: 365-379.
Peremarti et al. "Promoter diversity in multigene transformation," Plant Mol. Biol. (2010) 73:363-378.
Sambrook, et al., Molecular Cloning: A Laboratory Manual, Third Edition, Cold Spring Harbor Press, N.Y., 2001.
Jones et al., 1994 Science 266:789.
Martin et al., 1993 Science 262:1432.
Mindrinos et al., 1994 Cell 78:1089.
Geiser et al., 1986 Gene 48:109.
Estruch et al. (1996) Proc. Natl. Acad. Sci. 93:5389-94.
Van Damme et al., 1994 Plant Molec. Biol. 24:825.
Abe et al., 1987 J. Biol. Chem. 262:16793.
Huub et al., 1993 Plant Molec. Biol. 21:985.
Sumitani et al., 1993 Biosci. Biotech. Biochem. 57:1243.
Hammock et al., 1990 Nature 344:458.
Reagan, 1994, "Expression Cloning of an Insect Diuretic Hormone Receptor," J. Biol. Chem. vol. 269, No. 1, 9-12.
Pratt, 1989.
Pang, 1992 Gene 116:165.
Kramer et al., 1993 Insect Molec. Biol. 23:691.
Kawalleck et al., 1993 Plant Molec. Biol. 21:673.
Botella et al., 1994 Plant Molec. Biol. 24:757.
Griess et al., 1994 Plant Physiol. 104:1467.
Jaynes et al., "Expression of a Cecropin B lytic peptide analog in transgenic tobacco confers enhanced resistance to bacterial wilt caused by *Pseudomonas solanacearum*,"Plant Sci. 89:43 (1993).
Beachy et al. (1990) Ann. Rev. Phytopathol. 28:451.
Taylor et al. (1994) Abstract #497, Seventh Int'l. Symposium on Molecular Plant-Microbe Interactions.
Tavladoraki et al. (1993) Nature 266:469.
Lamb et al., "Emerging strategies for enhancing crop resistance to microbial pathogens," Bio/Technology (1992) 10:1436-1445.
Toubart et al., "Cloning and characterization of the gene encoding the endopolygalacturonase-inhiiting protein (PGIP) of *Phaseolus vulgaris* L.," The Plant Journal, 2(3), 367-373.
Logemann et al., "Expression of a Barley Ribosome-Inactivating Protein Leads to Incrased Fungal Protection in Transgenic Tobacco Plants," Bio/Technology (Mar. 1992), 10:305-308.
Lee et al., 1988 EMBOJ. 7:1241.
Miki et al., 1990 Theor. Appl. Genet. 80:449.
De Greef et al., "Evaluation of Herbicide Resistance in Transgenic Crops Under Field Conditions," Bio/Technology (1989) 7:61-64.
Marshall et al. (1992) Theor. Appl. Genet. 83:435.
Przibilla et al. (1991) Plant Cell 3:169.
Hayes et al. (1992) Biochem. J. 285:173.
Brusslan and Haselkorn, "Resistance of the photosystemII herbicide diuron is dominant to sensitivity in the cyanobacterium *Synechococcus* sp. PCC7942," The EMBO Journal. 1989, 8(4): 1237-1245.
Knutzon et al., "Modification of *Brassica* seed oil by antisense expression of a staroyl-acyl carrier proteindesaturase gene," Proc. Nat. Acad. Sci. USA (Apr. 1992) 89:2624-2628.
Van Hartingsveldt et al., 1993, Gene 127:87.
Raboy et al., 1990, Maydica 35:383.
Shiroza et al., "Sequence Analysis of the *Streptococcus mutans* Fructosyltransferase Gene and Flanking Regions,", J. Bacteriol., (1988) 170:810.
Steinmetz et al., "The DNA sequence of the gene for the secreted *Bacillus subtilis* enzyme levansucrase and its genetic control sites," Mol. Gen. Genel. (1985) 200:220-228.
Pen et al., "Production of Active *Bacillus Licheniformis* Alpha-Amylase in Tobacco and its Application in Starch Liquifaction," Bio/Technology (1992) 10:292.
Elliot et al., 1993.
Sogaard et al., 1993, J. Biol. Chem. 268:22480.
Fisher et al., "Starch Branching Enzyme II from Maize Endosperm," Plant Physiol. 102:1045-1046 (1993).
Klein et al., 1987, Nature 327:70-73.
Chung et al. (2006) *Trends Plant Sci.* 11(1):1-4.
Rios et al. "Rapid identification of *Arabidopsis* insertion mutants by non-radioactive detection of T-DNA tagged genes," The Plant Journal (2002) 32:243-53.
Goto-Fumiyuki et al., *Nature Biotech* 17:282-286 (1999).
Miki et al., Methods in Plant Molecular Biology and Biotechnology, Glick, B. R. and Thompson, J. E. Eds., CRC Press, Inc., Boca Raton, pp. 67-88 (1993). (Book).
Gruber et al., Methods in Plant Molecular Biology and Biotechnology, Glick, B. R. and Thompson, J. E. Eds., CRC Press, Inc., Boca Raton, pp. 89-119 (1993). (Book).
Ausubel et al. (1995).
Shagin, D. A., "GFP-like Porteins as ubiquitous Metazoan Superfamily: Evolution of Functional Features and Structural Complexity," *Mol Biol Evol.* (2004), 21;841-50.
Vancanneyt, G., (1990) *Mol Gen Genet.* 220;245-50.

(56) References Cited

OTHER PUBLICATIONS

Wehrmann et al., "The similarities of bar and pat gene products make them equally applicable for plant engineers," Nature Biotechnology (1996) 14:1274-1278.
Vega et al., 2008, *Plant Cell Rep* 27:297-305.
International Search Report and Written Opinion, International Application No. PCT/US2014/072913, dated Jun. 8, 2015, 11 pages.
Extended European Search Report, European Application No. 14875980.6-1410 / 3090045, dated May 4, 2017, 9 pages.
Shen et al., "A Primary Study of High Performance Transgenic Rice Through Maize UBI-1 Promoter Fusing Selective Maker Gene", Pakistan Journal of Botany, Jan. 1, 2012, pp. 501-506.
Rooke et al., "Marker gene expression driven by the maize ubiquitin promoter in transgenic wheat", Annals of Applied Biology, vol. 136, No. 2, Apr. 1, 2000, pp. 167-172.
Mann et al., "Switchgrass (*Panicum virgatum* L.) polyubiquitin gene (PvUbi1 and PvUbi2) promoters for use in plant transformation", BMC Biotechnology, Biomed Central Ltd., London, GB, vol. 11, No. 1, Jul. 11, 2011, p. 74.

\* cited by examiner

FIG. 3

GTGCAGCGTGACCCGGTCGTGCCCCTCTCTAGAGATAATGAGCATTGCATGTC
TAAGTTATAAAAAATTACCACATATTTTTTTGTCACACTTGTTTGAAGTGCA
GTTTATCTATCTTTATACATATATTTAAACTTTACTCTACGAATAATATAATCT
ATAGTACTACAATAATATCAGTGTTTTAGAGAATCATATAAATGAACAGTTA
GACATGGTCTAAAGGACAATTGAGTATTTTGACAACAGGACTCTACAGTTTT
ATCTTTTAGTGTGCATGTGTTCTCCTTTTTTTTGCAAATAGCTTCACCTATA
TAATACTTCATCCATTTTATTAGTACATCCATTTAGGGTTTAGGGTTAATGGTT
TTTATAGACTAATTTTTTAGTACATCTATTTTATTCTATTTTAGCCTCTAAATT
AAGAAAACTAAAACTCTATTTTAGTTTTTTTATTTAATAGTTTAGATATAAAA
TAGAATAAAATAAAGTGACTAAAAATTAAACAAATACCCTTTAAGAAATTAA
AAAAACTAAGGAAACATTTTTCTTGTTTCGAGTAGATAATGCCAGCCTGTTAA
ACGCCGTCGACGAGTCTAACGGACACCAACCAGCGAACCAGCAGCGTCGCGT
CGGGCCAAGCGAAGCAGACGGCACGGCATCTCTGTCGCTGCCTCTGGACCCC
TCTCGAGAGTTCCGCTCCACCGTTGGACTTGCTCCGCTGTCGGCATCCAGAAA
TTGCGTGGCGGAGCGGCAGACGTGAGCCGGCACGGCAGGCGGCCTCCTCCTC
CTCTCACGGCACCGGCAGCTACGGGGGATTCCTTTCCCACCGCTCCTTCGCTT
TCCCTTCCTCGCCCGCCGTAATAAATAGACACCCCCTCCACACCCTCTTTCCC
CAACCTCGTGTTGTTCGGAGCGCACACACACACAACCAGATCTCCCCCAAAT
CCACCCGTCGGCACCTCCGCTTCAAGgtacgccgctcgtcctcccccccccccccctctctaccttctct
agatcggcgttccggtccatgcatggttagggcccggtagttctacttctgttcatgtttgtgttagatccgtgtttgtgttagatccgt
gctgctagccgttcgtacacggatgcgacctgtacgtcagacacgtctgattgctaacttgccagtgtttctctttggggaatcctgg
gatggctctagccgttccgcagacgggatcgatttcatgatttttttttgtttcgttgcatagggtttggtttgcccttttcctttatttcaat
atatgccgtgcacttgtttgtcgggtcatcttttcatgctttttttttgtcttggttgtgatgatgtggtctggttgggcggtcgttctagatc
ggagtagaattctgtttcaaactacctggtggatttattaattttggatctgtatgtgtgtgccatacatattcatagttacgaattgaag
atgatggatggaaatatcgatctaggataggtatacatgttgatgcgggttttactgatgcatatacagagatgcttttgttcgcttg
gttgtgatgatgtggtgtggttgggcggtcgttcattcgttctagatcggagtagaatactgtttcaaactacctggtgtatttattaatt
ttggaactgtatgtgtgtgtcatacatcttcatagttacgagtttaagatggatggaaatatcgatctaggataggtatacatgttgatg
tgggtttactgatgcatatacatgatggcatatgcagcatctattcatatgctctaaccttgagtacctatctattataataaacaagta
tgttttataattatttcgatcttgatatacttggatgatggcatatgcagcagctatatgtggatttttttagccctgccttcatacgctattt
atttgcttggtactgtttcttttgtcgatgctcaccctgttgtttggtgttacttctgca

FIG. 4

CCCGGTCGTGCCCCTCTCTAGAGATAAAGAGCATTGCATGTCTAAAGTATAA
AAAATTACCACATATTTTTTGTCACACTTATTTGAAGTGTAGTTTATCTATCT
CTATACATATATTTAAACTTCACTCTACAAATAATATAGTCTATAATACTAAA
ATAATATTAGTGTTTTAGAGGATCATATAAATAAACTGCTAGACATGGTCTAA
AGGATAATTGAATATTTTGACAATCTACAGTTTTATCTTTTTAGTGTGCATGT
GATCTCTCTGTTTTTTTTGCAAATAGCTTGACCTATATAATACTTCATCCATTT
TATTAGTACATCCATTTAGGATTTAGGGTTGATGGTTTCTATAGACTAATTTTT
AGTACATCCATTTTATTCTTTTTAGTCTCTAATTTTTTTAAAACTAAAACTCTA
TTTTAGTTTTTTATTTAATAATTTAGATATAAAATGAAATAAAATAAATTGAC
TACAAATAAAACAAATACCCTTTAAGAAATAAAAAAACTAAGCAAACATTTT
TCTTGTTTCGAGTAGATAATGACAGGCTGTTCAACGCCGTCGACGAGTCTAAC
GGACACCAACCAGCGAACCAGCAGCGTCGCGTCGGGCCAAGCGAAGCAGAC
GGCACGGCATCTCTGTAGCTGCCTCTGGACCCCTCTCGAGAGTTCCGCTCCAC
CGTTGGACTTGCTCCGCTGTCGGCATCCAGAAATTGCGTGGCGGAGCGGCAG
ACGTGAGGCGGCACGGCAGGCGGCCTCTTCCTCCTCTCACGGCACCGGCAGC
TACGGGGGATTCCTTTCCCACCGCTCCTTCGCTTTCCCTTCCTCGCCCGCCGTA
ATAAATAGACACCCCCTCCACACCCTCTTTCCCCAACCTCGTGTTCGTTCGGA
GCGCACACACACGCAACCAGATCTCCCCCAAATCCAGCCGTCGGCACCTCCG
CTTCAAGgtacgccgctcatcctcccccccccctctctctaccttctctagatcggcgatccggtccatggttagggcccgg
tagttctacttctgttcatgtttgtgttagagcaaacatgttcatgttcatgtttgtgatgatgtggtctggttgggcggtcgttctagatc
ggagtaggatactgtttcaagctacctggtggatttattaattttgtatctgtatgtgtgtgccatacatcttcatagttacgagtttaag
atgatggatggaaatatcgatctaggataggtatacatgttgatgcgggttttactgatgcatatacagagatgctttttttctcgcttg
gttgtgatgatatggtctggttgggcggtcgttctagatcggagtagaatactgtttcaaactacctggtggatttattaaagggtcgt
tctagatcggagtagaatactgtttcaaactacctggtggatttattaaaggatctgtatgtatgtgcctacatcttcatagttacgagtt
taagatgatggatggaaatatcgatctaggataggtatacatgttgatgcgggttttactgatgcatatacagagatgctttttttcgct
tggttgtgatgatgtggtctggttgggcggtcgttctagatcggagtagaatactgtttcaaactacctggtggatttattaattttgtat
ctttatgtgtgtgccatacatcttcatagttacgagtttaagatgatggatggaaatattgatctaggataggtatacatgttgatgtgg
gttttactgatgcatatacatgatggcatatgcggcatctattcatatgctctaaccttgagtacctatctattataataaacaagtatgtt
ttataattattttgatcttgatatacttggatgatggcatatgcagcagctatatgtggatttttttagccctgccttcatacgctatttatttg
cttggtactgtttcttttgtccgatgctcaccctgttgtttggtgttacttctgcag

FIG. 5

```
                                              1                              30
Zea mays c.v. B104 Ubi-1 Upstream      (1)   ------------CCCGGTGGTGCCCCTCTCT
Zea mays c.v. B73  Ubi-1 Upstream      (1)   GTGCAGCGTGACCCGGTGGTGCCCCTCTCT
                                             31                             60
Zea mays c.v. B104 Ubi-1 Upstream     (20)   AGAGATAAAGAGCATTGCATGTCTAAAGTA
Zea mays c.v. B73  Ubi-1 Upstream     (31)   AGAGATAATGAGCATTGCATGTCTAAGTTA
                                             61                             90
Zea mays c.v. B104 Ubi-1 Upstream     (50)   TAAAAAATTACCACATATTTTTT-GTCAC
Zea mays c.v. B73  Ubi-1 Upstream     (61)   TAAAAAATTACCACATATTTTTTCTCAC
                                             91                            120
Zea mays c.v. B104 Ubi-1 Upstream     (79)   ACTTATTGAAGTGTAGTTTATCTATCTC
Zea mays c.v. B73  Ubi-1 Upstream     (91)   ACTTGTTGAAGTCAGTTTATCTATCTT
                                            121                            150
Zea mays c.v. B104 Ubi-1 Upstream    (109)   ATACATATATTTAAACTTCACTCTACAAAT
Zea mays c.v. B73  Ubi-1 Upstream    (121)   ATACATATATTTAAACTTTACTCTACGAAT
                                            151                            180
Zea mays c.v. B104 Ubi-1 Upstream    (139)   AATATAGTCTATAATACTAAAATAATATTA
Zea mays c.v. B73  Ubi-1 Upstream    (151)   AATATAATCTATAGTACTACAATAATATCA
                                            181                            210
Zea mays c.v. B104 Ubi-1 Upstream    (169)   GTGTTTTAGAGGATCATATAAATAAACTGC
Zea mays c.v. B73  Ubi-1 Upstream    (181)   GTGTTTTAGACAATCATATAAATGAACAGT
                                            211                            240
Zea mays c.v. B104 Ubi-1 Upstream    (199)   TAGACATGGTCTAAAGGATAATTGAATATT
Zea mays c.v. B73  Ubi-1 Upstream    (211)   TAGACATGGTCTAAAGGACAATTGAGTATT
                                            241                            270
Zea mays c.v. B104 Ubi-1 Upstream    (229)   TTGACAA------TCTACAGTTTTATCTT
Zea mays c.v. B73  Ubi-1 Upstream    (241)   TTGACAACAGGACTCTACAGTTTTATCTT
                                            271                            300
Zea mays c.v. B104 Ubi-1 Upstream    (253)   TTAGTGTGCATGTGATTTCTGTTTTTT
Zea mays c.v. B73  Ubi-1 Upstream    (271)   TTAGTGTGCATGTGTTCTC-CT-TTTTTTT
                                            301                            330
Zea mays c.v. B104 Ubi-1 Upstream    (283)   TGCAAATAGCTTGACCTATATAATACTTCA
Zea mays c.v. B73  Ubi-1 Upstream    (299)   TGCAAATAGCTTCACCTATATAATACTTCA
                                            331                            360
Zea mays c.v. B104 Ubi-1 Upstream    (313)   TCCATTTTATTAGTACATCCATTTAGGAT
Zea mays c.v. B73  Ubi-1 Upstream    (329)   TCCATTTTATTAGTACATCCATTTAGGGT
                                            361                            390
Zea mays c.v. B104 Ubi-1 Upstream    (343)   TAGGGTTGATGGTTTCTATAGACTAATTTT
Zea mays c.v. B73  Ubi-1 Upstream    (359)   TAGGGTTAATGGTTTTTATAGACTAATTTT
                                            391                            420
Zea mays c.v. B104 Ubi-1 Upstream    (373)   T--AGTACATCCATTTTATTCT-TTTTAGT
Zea mays c.v. B73  Ubi-1 Upstream    (389)   TTTAGTACATCTATTTTATTCTATTTTAGC
                                            421                            450
Zea mays c.v. B104 Ubi-1 Upstream    (400)   CTCTAATTTTTTTAAAATAAAACTCTATT
Zea mays c.v. B73  Ubi-1 Upstream    (419)   CTCTAAATTAAG-AAAACTAAAACTCTATT
                                            451                            480
Zea mays c.v. B104 Ubi-1 Upstream    (430)   TTAGTTTTT-ATTTAATAATTTAGATATA
Zea mays c.v. B73  Ubi-1 Upstream    (448)   TTAGTTTTTTATTTAATAGTTTAGATATA
                                            481                            510
Zea mays c.v. B104 Ubi-1 Upstream    (459)   AAATGAAATAAAATAAATGACTACAAATA
Zea mays c.v. B73  Ubi-1 Upstream    (478)   AAATAGAATAAAATAAAGTGACTAAAATT
                                            511                            540
Zea mays c.v. B104 Ubi-1 Upstream    (489)   AAACAAATACCCTTTAAGAAAT-AAAAAAA
Zea mays c.v. B73  Ubi-1 Upstream    (508)   AAACAAATACCCTTTAAGAAATTAAAAAAA
```

FIG. 5 (continued)

```
                                              541                           570
Zea mays c.v. B104 Ubi-1 Upstream     (518)   CTAAGCAAACATTTTCTTGTTTGAGTAC
Zea mays c.v. B73  Ubi-1 Upstream     (538)   CTAAGGAAACATTTTCTTGTTTGAGTAC
                                              571                           600
Zea mays c.v. B104 Ubi-1 Upstream     (548)   ATAATGACAGGCTGTTCAACGCGTCGACG
Zea mays c.v. B73  Ubi-1 Upstream     (568)   ATAATGCCAGCTTGTTAAACGCCGTCGACG
                                              601                           630
Zea mays c.v. B104 Ubi-1 Upstream     (578)   AGTTTAACGGACACCAACCAGCGAACCAGC
Zea mays c.v. B73  Ubi-1 Upstream     (598)   AGTCTAACGGACACCAACCAGCGAACCAGC
                                              631                           660
Zea mays c.v. B104 Ubi-1 Upstream     (608)   AGCGTCCGTCGGGCCAAGCGAAGCAGACG
Zea mays c.v. B73  Ubi-1 Upstream     (628)   AGCGTCCGTCGGGCCAAGCGAAGCAGACG
                                              661                           690
Zea mays c.v. B104 Ubi-1 Upstream     (638)   GCACGGCATTCTGTAGCTGCTCTGGACC
Zea mays c.v. B73  Ubi-1 Upstream     (658)   GCACGGCATCCTGCGCTGCCTCTGGACC
                                              691                           720
Zea mays c.v. B104 Ubi-1 Upstream     (668)   CCTCTGAGAGTTCGGCTCCACCGTTGGAC
Zea mays c.v. B73  Ubi-1 Upstream     (688)   CCTCTGAGAGTTCGGCTCCACCGTTGGAC
                                              721                           750
Zea mays c.v. B104 Ubi-1 Upstream     (698)   TTGCTCGGTGTCGGCATCCAGAAATTGCG
Zea mays c.v. B73  Ubi-1 Upstream     (718)   TTGCTCGGTGTCGGCATCCAGAAATTGCG
                                              751                           780
Zea mays c.v. B104 Ubi-1 Upstream     (728)   TGGCGAGCGGCAGACGTGAGGCGGCACGG
Zea mays c.v. B73  Ubi-1 Upstream     (748)   TGGCGAGCGGCAGACGTGAGCGGCACGG
                                              781                           810
Zea mays c.v. B104 Ubi-1 Upstream     (758)   CAGGCGGCCTTCCTCCTCCTCACGGCACC
Zea mays c.v. B73  Ubi-1 Upstream     (778)   CAGGCGGCCTCCCTCCTCCTCACGGCACC
                                              811                           840
Zea mays c.v. B104 Ubi-1 Upstream     (788)   GGCAGCTACGGGGATTCTTTCCACGGC
Zea mays c.v. B73  Ubi-1 Upstream     (808)   GGCAGCTACGGGGATTCTTTCCACGGC
                                              841                           870
Zea mays c.v. B104 Ubi-1 Upstream     (818)   TCCTTGCTTTCCTTCCTCGCCGGCGTA
Zea mays c.v. B73  Ubi-1 Upstream     (838)   TCCTTGCTTTCCTTCCTCGCCGGCGTA
                                              871                     899
Zea mays c.v. B104 Ubi-1 Upstream     (848)   ATAAATAGACACCCCTCCACACCCTCTT
Zea mays c.v. B73  Ubi-1 Upstream     (868)   ATAAATAGACACCCCTCCACACCCTCTT
```

FIG. 6

```
                                              1                              30
Zea mays c.v. B104 Ubi-1 Leader    (1)   TCCCCAACCTCGTGTTCGTTCGGAGCGCAC
 Zea mays c.v. B73 Ubi-1 Leader    (1)   TCCCCAACCTCGTGTT-GTTCGGAGCGCAC
                                             31                              60
Zea mays c.v. B104 Ubi-1 Leader    (31)  ACACACGCAACCAGATCTCCCCCAAATCCA
 Zea mays c.v. B73 Ubi-1 Leader    (30)  ACACACACAACCAGATCTCCCCCAAATCCA
                                             61                    83
Zea mays c.v. B104 Ubi-1 Leader    (61)  GCCCGTCGGCACCTCCGCTTCAAG
 Zea mays c.v. B73 Ubi-1 Leader    (60)  CCCGTCGGCACCTCCGCTTCAAG
```

FIG. 7

```
                                            1                              30
Zea mays c.v. B73 Ubi-1 Intron    (1)    GTACGCCGCTCGTCCTCCCCCCCCCCCCC
Zea mays c.v. B104 Ubi-1 Intron   (1)    GTACGCCGCTCATCCTCCCCCCCCCCTC--
                                           31                             60
Zea mays c.v. B73 Ubi-1 Intron   (31)    CTCTCTACCTTCTCTAGATCGGCGTTCCG
Zea mays c.v. B104 Ubi-1 Intron  (29)    -TCTCTACCTTCTCTAGATCGGCGATCCG
                                           61                             90
Zea mays c.v. B73 Ubi-1 Intron   (61)    GCCATGCATGGTTAGGGCCCGGTAGTTCTA
Zea mays c.v. B104 Ubi-1 Intron  (58)    GCCATG----GTTAGGGCCCGGTAGTTCTA
                                           91                            120
Zea mays c.v. B73 Ubi-1 Intron   (91)    CTTCTGTTCATGTTTGTGTTAGATC-----
Zea mays c.v. B104 Ubi-1 Intron  (84)    CTTCTGTTCATGTTTGTGTTAGAGCAAACA
                                          121                            150
Zea mays c.v. B73 Ubi-1 Intron  (116)    ----------CGTGTTTGTGTTAGATCCGT
Zea mays c.v. B104 Ubi-1 Intron (114)    TGTTCATGTTCATGTTTGTGAT-GATGTGG
                                          151                            180
Zea mays c.v. B73 Ubi-1 Intron  (136)    GTTCCTAG--CGTTCGTACACGGATGCCAC
Zea mays c.v. B104 Ubi-1 Intron (143)    TCTGGTTGGGCGGTCCTTCTAG-ATCGGAG
                                          181                            210
Zea mays c.v. B73 Ubi-1 Intron  (164)    CTG--TAC-GTCAGACACGTTCTGATTGCT
Zea mays c.v. B104 Ubi-1 Intron (172)    TAGGATACTGTTTCAAGCTACCTGGTGGAT
                                          211                            240
Zea mays c.v. B73 Ubi-1 Intron  (191)    AACTGCCAGTGTTCTCTTGGGGAATCC
Zea mays c.v. B104 Ubi-1 Intron (202)    TTATGAATTTGCTATCTGTATGTGTGCC
                                          241                            270
Zea mays c.v. B73 Ubi-1 Intron  (221)    TGGGATGGCTCTAGC--CGTTCCGCAGACG
Zea mays c.v. B104 Ubi-1 Intron (232)    ATACATCTTCATAGTTACCAGTTTAACATG
                                          271                            300
Zea mays c.v. B73 Ubi-1 Intron  (249)    --GCATCGATTTCATGATTTTTTT--GTT
Zea mays c.v. B104 Ubi-1 Intron (262)    ATGCATGCAAATCGATCTAGGATAGCTA
                                          301                            330
Zea mays c.v. B73 Ubi-1 Intron  (275)    GC---GTTGCATAGGGTTTGGTG--------
Zea mays c.v. B104 Ubi-1 Intron (292)    GACATGTTCATGCGGGTTTACGGATGCAT
                                          331                            360
Zea mays c.v. B73 Ubi-1 Intron  (295)    ---------TGGCCTTTCCGTTATTTCAA
Zea mays c.v. B104 Ubi-1 Intron (322)    ATACAGAGATGGTTTTTTTCTCGCTTGGTT
                                          361                            390
Zea mays c.v. B73 Ubi-1 Intron  (316)    TATAGCCGGCAGTGTTTGTCGGGTCAG
Zea mays c.v. B104 Ubi-1 Intron (352)    GTGAGGATAGGTGTGGTTGGCGGTCGTT
                                          391                            420
Zea mays c.v. B73 Ubi-1 Intron  (346)    GTTTCATGCTGTTTTTGCCGGGTTGTG
Zea mays c.v. B104 Ubi-1 Intron (382)    GCAGATCGGAGGAGAATACTGTTCAAACT
                                          421                            450
Zea mays c.v. B73 Ubi-1 Intron  (376)    GTGATGTGGTCGGGTGGGCGGTCGTTCTA
Zea mays c.v. B104 Ubi-1 Intron (412)    ACCTGGTGGATTTATTAAAGGGTCGTTCTA
                                          451                            480
Zea mays c.v. B73 Ubi-1 Intron  (406)    GATCGGAGTAGAATTCTGTTTCAAACTAC
Zea mays c.v. B104 Ubi-1 Intron (442)    GATCGGAGTAGAATACTGTTTCAAACTACC
                                          481                            510
Zea mays c.v. B73 Ubi-1 Intron  (436)    GGTGGATTTATTAATTTTGGATCTGTATG
Zea mays c.v. B104 Ubi-1 Intron (472)    GGTGGATTTATTAAA----GGATCTGTATG
                                          511                            540
Zea mays c.v. B73 Ubi-1 Intron  (466)    GTTTGCCATACATTCATAGTTACCGAT
Zea mays c.v. B104 Ubi-1 Intron (499)    ATTTGCC-TACATCTTCATAGTTACCAGT
```

FIG. 7 (continued)

```
                                          541                        570
Zea mays c.v. B73 Ubi-1 Intron    (496)   TGAAGATGATGGATGGAAATATCGATCTAG
Zea mays c.v. B104 Ubi-1 Intron   (528)   TTAAGATGATGGATGGAAATATCGATCTAG
                                          571                        600
Zea mays c.v. B73 Ubi-1 Intron    (526)   GATAGGTATACATGTTGATGCGGGTTTTAC
Zea mays c.v. B104 Ubi-1 Intron   (558)   GATAGGTATACATGTTGATGCGGGTTTTAC
                                          601                        630
Zea mays c.v. B73 Ubi-1 Intron    (556)   TGATGCATATACAGAGATGCTTTTTGTTCG
Zea mays c.v. B104 Ubi-1 Intron   (588)   TGATGCATATACAGAGATGCTTTTT-TTCG
                                          631                        660
Zea mays c.v. B73 Ubi-1 Intron    (586)   TTGGTTGTGATGATGTGGTGTGGTTGGGC
Zea mays c.v. B104 Ubi-1 Intron   (617)   TTGGTTGTGATGATGTGGTCTGGTTGGGC
                                          661                        690
Zea mays c.v. B73 Ubi-1 Intron    (616)   GGTCGTTCATTCGTTCTAGATCGGAGTAGA
Zea mays c.v. B104 Ubi-1 Intron   (647)   GGT--------CGTTCTAGATCGGAGTAGA
                                          691                        720
Zea mays c.v. B73 Ubi-1 Intron    (646)   ATACTGTTCAAACTACCTGGTGTATTTAT
Zea mays c.v. B104 Ubi-1 Intron   (669)   ATACTGTTCAAACTACCTGGTGGATTTAT
                                          721                        750
Zea mays c.v. B73 Ubi-1 Intron    (676)   TAATTTTGGAACTGTATCTGTGTGTCATAC
Zea mays c.v. B104 Ubi-1 Intron   (699)   TAATTTTGTATCTTATGTGTGTGCCATAC
                                          751                        780
Zea mays c.v. B73 Ubi-1 Intron    (706)   ATCTTCATAGTTACGAGTTTAAGATG---G
Zea mays c.v. B104 Ubi-1 Intron   (729)   ATCTTCATAGTTACGAGTTTAAGATGATGG
                                          781                        810
Zea mays c.v. B73 Ubi-1 Intron    (733)   ATGGAAATATCGATCTAGGATAGGTATACA
Zea mays c.v. B104 Ubi-1 Intron   (759)   ATGGAAATATTGATCTAGGATAGGTATACA
                                          811                        840
Zea mays c.v. B73 Ubi-1 Intron    (763)   TGTTGATGTGGGTTTTACTGATGCATATAC
Zea mays c.v. B104 Ubi-1 Intron   (789)   TGTTGATGTGGGTTTTACTGATGCATATAC
                                          841                        870
Zea mays c.v. B73 Ubi-1 Intron    (793)   ATGATGGCATATGCAGCATTTATTCATATG
Zea mays c.v. B104 Ubi-1 Intron   (819)   ATGATGGCATATGCGGCATTTATTCATATG
                                          871                        900
Zea mays c.v. B73 Ubi-1 Intron    (823)   GTCTAACCTTGAGTACCTATCTATTATAAT
Zea mays c.v. B104 Ubi-1 Intron   (849)   GTTTAACCTTGAGTACCTATCTATTATAAT
                                          901                        930
Zea mays c.v. B73 Ubi-1 Intron    (853)   AAACAAGTATGTTTATAATTATTTCGAT
Zea mays c.v. B104 Ubi-1 Intron   (879)   AAACAAGTATGTTTATAATTATTTTGATC
                                          931                        960
Zea mays c.v. B73 Ubi-1 Intron    (883)   TTGATATACTTGGATGATGGCATATGCAGC
Zea mays c.v. B104 Ubi-1 Intron   (909)   TTGATATACTTGGATGATGGCATATGCAGC
                                          961                        990
Zea mays c.v. B73 Ubi-1 Intron    (913)   AGCTATATGTGGATTTTTTAGCCCTGCCT
Zea mays c.v. B104 Ubi-1 Intron   (939)   AGCTATATGTGGATTTTT-AGCCCTGCCT
                                          991                       1020
Zea mays c.v. B73 Ubi-1 Intron    (943)   TCATACGCTATTTATTTGCTTGGTACTGT
Zea mays c.v. B104 Ubi-1 Intron   (968)   TCATACGCTATTTATTTGCTTGGTACTGT
                                          1021                      1050
Zea mays c.v. B73 Ubi-1 Intron    (973)   TCTTTTGTC-GATGCTCAGCCTGTTGTTTG
Zea mays c.v. B104 Ubi-1 Intron   (998)   TCTTTTGTCCGATGCTCACCCTGTTGTTTG
                                          1051      1065
Zea mays c.v. B73 Ubi-1 Intron    (1002)  GTGTTACTTCTGCA-
Zea mays c.v. B104 Ubi-1 Intron   (1028)  GTGTTACTTCTGCAG
```

105745    105748

105745    Negative Control    105748

SEQUENCE LISTING

<160> NUMBER OF SEQ ID NOS: 19

<210> SEQ ID NO 1
<211> LENGTH: 1993
<212> TYPE: DNA
<213> ORGANISM: Zea mays

<400> SEQUENCE: 1

```
gtgcagcgtg acccggtcgt gcccctctct agagataatg agcattgcat gtctaagtta      60
taaaaaatta ccacatattt tttttgtcac acttgtttga agtgcagttt atctatcttt     120
atacatatat ttaaacttta ctctacgaat aatataatct atagtactac aataatatca     180
gtgttttaga gaatcatata aatgaacagt tagacatggt ctaaaggaca attgagtatt     240
ttgacaacag gactctacag ttttatcttt ttagtgtgca tgtgttctcc tttttttttg     300
caaatagctt cacctatata atacttcatc cattttatta gtacatccat ttagggttta     360
gggttaatgg tttttataga ctaattttt tagtacatct attttattct attttagcct      420
ctaaattaag aaaactaaaa ctctatttta gttttttat ttaatagttt agatataaaa      480
tagaataaaa taaagtgact aaaaattaaa caaatacccct ttaagaaatt aaaaaaacta    540
aggaaacatt tttcttgttt cgagtagata atgccagcct gttaaacgcc gtcgacgagt     600
ctaacggaca ccaaccagcg aaccagcagc gtcgcgtcgg gccaagcgaa gcagacggca     660
cggcatctct gtcgctgcct ctggacccct ctcgagagtt ccgctccacc gttggacttg     720
ctccgctgtc ggcatccaga aattgcgtgg cggagcggca gacgtgagcc ggcacggcag     780
gcggcctcct cctcctctca cggcaccggc agctacgggg gattcctttc ccaccgctcc     840
ttcgctttcc cttcctcgcc cgccgtaata aatagacacc ccctccacac cctctttccc     900
caacctcgtg ttgttcggag cgcacacaca cacaaccaga tctcccccaa atccacccgt     960
cggcacctcc gcttcaaggt acgccgctcg tcctccccc cccccccct ctctaccttc     1020 tctagatcgg cgttccggtc catgcatggt tagggcccgg tagttctact tctgttcatg    1080
tttgtgttag atccgtgttt gtgttagatc cgtgctgcta gcgttcgtac acggatgcga    1140
cctgtacgtc agacacgttc tgattgctaa cttgccagtg tttctctttg gggaatcctg    1200
ggatggctct agccgttccg cagacgggat cgatttcatg attttttttg tttcgttgca    1260
tagggtttgg tttgcccttt tcctttattt caatatatgc cgtgcacttg tttgtcgggt    1320
catcttttca tgctttttt tgtcttggtt gtgatgatgt ggtctggttg ggcggtcgtt     1380
ctagatcgga gtagaattct gtttcaaact acctggtgga tttattaatt ttggatctgt    1440
atgtgtgtgc catacatatt catagttacg aattgaagat gatggatgga aatatcgatc    1500
taggataggt atacatgttg atgcgggttt tactgatgca tatacagaga tgcttttttgt   1560 tcgcttggtt gtgatgatgt ggtgtggttg ggcggtcgtt cattcgttct agatcggagt    1620
agaatactgt ttcaaactac ctggtgtatt tattaatttt ggaactgtat gtgtgtgtca    1680
tacatcttca tagttacgag tttaagatgg atggaaatat cgatctagga taggtataca    1740
```

```
tgttgatgtg ggttttactg atgcatatac atgatggcat atgcagcatc tattcatatg    1800
ctctaacctt gagtacctat ctattataat aaacaagtat gttttataat tatttcgatc    1860
ttgatatact tggatgatgg catatgcagc agctatatgt ggattttttt agccctgcct    1920
tcatacgcta tttatttgct tggtactgtt tcttttgtcg atgctcaccc tgttgtttgg    1980
tgttacttct gca                                                       1993

<210> SEQ ID NO 2
<211> LENGTH: 2001
<212> TYPE: DNA
<213> ORGANISM: Zea mays

<400> SEQUENCE: 2
cccggtcgtg cccctctcta gagataaaga gcattgcatg tctaaagtat aaaaaattac      60
cacatatttt tttgtcacac ttatttgaag tgtagtttat ctatctctat acatatattt     120
aaacttcact ctacaaataa tatagtctat aatactaaaa taatattagt gttttagagg     180
atcatataaa taaactgcta gacatggtct aaaggataat tgaatatttt gacaatctac     240
agttttatct ttttagtgtg catgtgatct ctctgttttt tttgcaaata gcttgaccta     300
tataatactt catccatttt attagtacat ccatttagga tttagggttg atggtttcta     360
tagactaatt tttagtacat ccatttatt cttttagtc tctaattttt ttaaaactaa       420
aactctattt tagttttta tttaataatt tagatataaa atgaaataaa ataaattgac      480
tacaaataaa acaaataccc tttaagaaat aaaaaaacta agcaaacatt tttcttgttt     540
cgagtagata atgacaggct gttcaacgcc gtcgacgagt ctaacggaca ccaaccagcg     600
aaccagcagc gtcgcgtcgg gccaagcgaa gcagacggca cggcatctct gtagctgcct     660
ctggacccct ctcgagagtt ccgctccacc gttggacttg ctccgctgtc ggcatccaga     720
aattgcgtgg cggagcggca gacgtgaggc ggcacggcag gcggcctctt cctcctctca     780
cggcaccggc agctacgggg gattcctttc ccaccgctcc ttcgctttcc cttcctcgcc     840
cgccgtaata aatagacacc cctccacac cctctttccc caacctcgtg ttcgttcgga      900
gcgcacacac acgcaaccag atctccccca aatccagccg tcggcaccctc cgcttcaagg    960 tacgccgctc atcctccccc cccctctct ctaccttctc tagatcggcg atccggtcca     1020
tggttagggc ccgtagttc tacttctgtt catgttgtg ttagagcaaa catgttcatg      1080
ttcatgtttg tgatgatgtg gtctggttgg gcggtcgttc tagatcggag taggatactg    1140
tttcaagcta cctggtggat ttattaattt tgtatctgta tgtgtgtgcc atacatcttc    1200
atagttacga gtttaagatg atggatggaa atatcgatct aggataggta tacatgttga    1260
tgcgggtttt actgatgcat atacagagat gctttttttc tcgcttggtt gtgatgatat    1320
ggtctggttg gcggtcgtt ctagatcgga gtagaatact gtttcaaact acctggtgga    1380
tttattaaag ggtcgttcta gatcggagta gaatactgtt tcaaactacc tggtggattt    1440
attaaaggat ctgtatgtat gtgcctacat cttcatagtt acgagtttaa gatgatggat    1500
ggaaatatcg atctaggata ggtatacatg ttgatgcggg ttttactgat gcatatacag    1560
agatgctttt tttcgcttgg ttgtgatgat gtggtctggt tgggcggtcg ttctagatcg    1620
gagtagaata ctgtttcaaa ctacctggtg gatttattaa ttttgtatct ttatgtgtgt    1680
gccatacatc ttcatagtta cgagtttaag atgatggatg gaaatattga tctaggatag    1740
gtatacatgt tgatgtgggt tttactgatg catatacatg atggcatatg cggcatctat    1800
tcatatgctc taaccttgag tacctatcta ttataaaaa caagtatgtt ttataattat    1860
```

| tttgatcttg atatacttgg atgatggcat atgcagcagc tatatgtgga ttttttagcc | 1920 |
| ctgccttcat acgctattta tttgcttggt actgtttctt ttgtccgatg ctcaccctgt | 1980 |
| tgtttggtgt tacttctgca g | 2001 |

<210> SEQ ID NO 3
<211> LENGTH: 896
<212> TYPE: DNA
<213> ORGANISM: Zea mays

<400> SEQUENCE: 3

| gtgcagcgtg acccggtcgt gcccctctct agagataatg agcattgcat gtctaagtta | 60 |
| taaaaaatta ccacatattt tttttgtcac acttgtttga agtgcagttt atctatcttt | 120 |
| atacatatat ttaaacttta ctctacgaat aatataatct atagtactac aataatatca | 180 |
| gtgttttaga gaatcatata aatgaacagt tagacatggt ctaaaggaca attgagtatt | 240 |
| ttgacaacag gactctacag ttttatcttt ttagtgtgca tgtgttctcc tttttttttg | 300 |
| caaatagctt cacctatata atacttcatc cattttatta gtacatccat ttagggttta | 360 |
| gggttaatgg ttttttataga ctaattttt tagtacatct attttattct attttagcct | 420 |
| ctaaattaag aaaactaaaa ctctatttta gttttttat ttaatagttt agatataaaa | 480 |
| tagaataaaa taaagtgact aaaaattaaa caaatacccct ttaagaaatt aaaaaaacta | 540 |
| aggaaacatt tttcttgttt cgagtagata atgccagcct gttaaacgcc gtcgacgagt | 600 |
| ctaacggaca ccaaccagcg aaccagcagc gtcgcgtcgg gccaagcgaa gcagacggca | 660 |
| cggcatctct gtcgctgcct ctggacccct ctcgagagtt ccgctccacc gttggacttg | 720 |
| ctccgctgtc ggcatccaga aattgcgtgg cggagcggca gacgtgagcc ggcacggcag | 780 |
| gcggcctcct cctcctctca cggcaccggc agctacgggg gattcctttc ccaccgctcc | 840 |
| ttcgctttcc cttcctcgcc cgccgtaata aatagacacc cctccacac cctctt | 896 |

<210> SEQ ID NO 4
<211> LENGTH: 876
<212> TYPE: DNA
<213> ORGANISM: Zea mays

<400> SEQUENCE: 4

| cccggtcgtg cccctctcta gagataaaga gcattgcatg tctaaagtat aaaaaattac | 60 |
| cacatatttt tttgtcacac ttatttgaag tgtagtttat ctatctctat acatatattt | 120 |
| aaacttcact ctacaaataa tatagtctat aatactaaaa taatattagt gttttagagg | 180 |
| atcatataaa taaactgcta gacatggtct aaaggataat tgaatatttt gacaatctac | 240 |
| agttttatct ttttagtgtg catgtgatct ctctgttttt tttgcaaata gcttgaccta | 300 |
| tataatactt catccatttt attagtacat ccatttagga tttaggggttg atggtttcta | 360 |
| tagactaatt tttagtacat ccattttatt ctttttagtc tctaattttt ttaaaactaa | 420 |
| aactctatttt tagtttttta tttaataatt tagatataaa atgaaataaa ataaattgac | 480 |
| tacaaataaa acaaataccc tttaagaaat aaaaaaacta agcaaacatt tttcttgttt | 540 |
| cgagtagata atgacaggct gttcaacgcc gtcgacgagt ctaacggaca ccaaccagcg | 600 |
| aaccagcagc gtcgcgtcgg gccaagcgaa gcagacggca cggcatctct gtagctgcct | 660 |
| ctggacccct ctcgagagtt ccgctccacc gttggacttg ctccgctgtc ggcatccaga | 720 |
| aattgcgtgg cggagcggca gacgtgaggc ggcacggcag gcggcctctt cctcctctca | 780 |

```
cggcaccggc agctacgggg gattcctttc ccaccgctcc ttcgctttcc cttcctcgcc    840
cgccgtaata aatagacacc ccctccacac cctctt                              876

<210> SEQ ID NO 5
<211> LENGTH: 82
<212> TYPE: DNA
<213> ORGANISM: Zea mays

<400> SEQUENCE: 5
tccccaacct cgtgttgttc ggagcgcaca cacacacaac cagatctccc ccaaatccac    60
ccgtcggcac ctccgcttca ag                                             82

<210> SEQ ID NO 6
<211> LENGTH: 83
<212> TYPE: DNA
<213> ORGANISM: Zea mays

<400> SEQUENCE: 6
tccccaacct cgtgttcgtt cggagcgcac acacacgcaa ccagatctcc cccaaatcca    60
gccgtcggca cctccgcttc aag                                            83

<210> SEQ ID NO 7
<211> LENGTH: 1015
<212> TYPE: DNA
<213> ORGANISM: Zea mays

<400> SEQUENCE: 7
gtacgccgct cgtcctcccc cccccccccc ctctctacct tctctagatc ggcgttccgg    60
tccatgcatg gttagggccc ggtagttcta cttctgttca tgtttgtgtt agatccgtgt    120
ttgtgttaga tccgtgctgc tagcgttcgt acacggatgc gacctgtacg tcagacacgt    180
tctgattgct aacttgccag tgtttctctt tggggaatcc tgggatggct ctagccgttc    240
cgcagacggg atcgatttca tgattttttt tgtttcgttg catagggttt ggtttgccct    300
tttcctttat ttcaatatat gccgtgcact tgtttgtcgg gtcatctttt catgcttttt    360
tttgtcttgg ttgtgatgat gtggtctggt tgggcggtcg ttctagatcg gagtagaatt    420
ctgtttcaaa ctacctggtg gatttattaa ttttggatct gtatgtgtgt gccatacata    480
ttcatagtta cgaattgaag atgatggatg gaaatatcga tctaggatag gtatacatgt    540
tgatgcgggt tttactgatg catatacaga gatgcttttt gttcgcttgg ttgtgatgat    600
gtggtgtggt tgggcggtcg ttcattcgtt ctagatcgga gtagaatact gtttcaaact    660
acctggtgta tttattaatt ttggaactgt atgtgtgtgt catacatctt catagttacg    720
agtttaagat ggatggaaat atcgatctag gataggtata catgttgatg tgggttttac    780
tgatgcatat acatgatggc atatgcagca tctattcata tgctctaacc ttgagtacct    840
atctattata ataaacaagt atgttttata attatttcga tcttgatata cttggatgat    900
ggcatatgca gcagctatat gtggattttt ttagccctgc cttcatacgc tatttatttg    960
cttggtactg tttcttttgt cgatgctcac cctgttgttt ggtgttactt ctgca         1015

<210> SEQ ID NO 8
<211> LENGTH: 1042
<212> TYPE: DNA
<213> ORGANISM: Zea mays

<400> SEQUENCE: 8
gtacgccgct catcctcccc ccccccctctc tctaccttct ctagatcggc gatccggtcc    60
```

```
atggttaggg cccggtagtt ctacttctgt tcatgtttgt gttagagcaa acatgttcat    120
gttcatgttt gtgatgatgt ggtctggttg ggcggtcgtt ctagatcgga gtaggatact    180
gtttcaagct acctggtgga tttattaatt ttgtatctgt atgtgtgtgc catacatctt    240
catagttacg agtttaagat gatggatgga aatatcgatc taggataggt atacatgttg    300
atgcgggttt tactgatgca tatacagaga tgctttttt ctcgcttggt tgtgatgata    360
tggtctggtt gggcggtcgt tctagatcgg agtagaatac tgtttcaaac tacctggtgg    420
atttattaaa gggtcgttct agatcggagt agaatactgt ttcaaactac ctggtggatt    480
tattaaagga tctgtatgta tgtgcctaca tcttcatagt tacgagttta agatgatgga    540
tggaaatatc gatctaggat aggtatacat gttgatgcgg gttttactga tgcatataca    600
gagatgcttt ttttcgcttg gttgtgatga tgtggtctgg ttgggcggtc gttctagatc    660
ggagtagaat actgtttcaa actacctggt ggatttatta attttgtatc tttatgtgtg    720
tgccatacat cttcatagtt acgagtttaa gatgatggat ggaaatattg atctaggata    780
ggtatacatg ttgatgtggg ttttactgat gcatatacat gatggcatat gcggcatcta    840
ttcatatgct ctaaccttga gtacctatct attataataa acaagtatgt tttataatta    900
ttttgatctt gatatacttg gatgatggca tatgcagcag ctatatgtgg attttttagc    960
cctgccttca tacgctatt attgcttgg tactgtttct tttgtccgat gctcaccctg    1020
ttgtttggtg ttacttctgc ag                                            1042
```

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 9

```
gctaccgcgg acccggtcgt gcccctctct agagataatg                          40
```

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 10

```
agtcaggtac cctgcagaag taacaccaaa caacag                              36
```

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 11

```
cgtgttggga aagaacttgg a                                              21
```

<210> SEQ ID NO 12
<211> LENGTH: 18
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 12
ccgtggttgg cttggtct                                                  18

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'FAM

<400> SEQUENCE: 13
cactccccac tgcct                                                     15

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tggcggacga cgacttgt                                                  18

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aaagtttgga ggctgccgt                                                 19

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'HEX

<400> SEQUENCE: 16
cgagcagacc gccgtgtact t                                              21

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acaagagtgg attgatgatc tagagaggt                                      29

<210> SEQ ID NO 18
```

```
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctttgatgcc tatgtgacac gtaaacagt                                    29

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'FAM

<400> SEQUENCE: 19
ggtgttgtgg ctggtattgc ttacgctgg                                    29
```

MAIZE UBIQUITIN PROMOTERS

CROSS-REFERENCE TO RELATED APPLICATIONS

This application claims the benefit under 35 USC § 119(e) of U.S. Provisional Application Ser. No. 61/922,522, filed on Dec. 31, 2013, the entire disclosure of which is incorporated herein by reference.

FIELD OF THE INVENTION

This invention is generally related to the field of plant molecular biology, and more specifically, to the field of expression of transgenes in plants.

BACKGROUND

Many plant species are capable of being transformed with transgenes to introduce agronomically desirable traits or characteristics. Plant species are developed and/or modified to have particular desirable traits. Generally, desirable traits include, for example, improving nutritional value quality, increasing yield, conferring pest or disease resistance, increasing drought and stress tolerance, improving horticultural qualities (e.g., pigmentation and growth), imparting herbicide resistance, enabling the production of industrially useful compounds and/or materials from the plant, and/or enabling the production of pharmaceuticals.

Transgenic plant species comprising multiple transgenes stacked at a single genomic locus are produced via plant transformation technologies. Plant transformation technologies result in the introduction of a transgene into a plant cell, recovery of a fertile transgenic plant that contains the stably integrated copy of the transgene in the plant genome, and subsequent transgene expression via transcription and translation of the plant genome results in transgenic plants that possess desirable traits and phenotypes. However, mechanisms that allow the production of transgenic plant species to highly express multiple transgenes engineered as a trait stack are desirable.

Likewise, mechanisms that allow the expression of a transgene within particular tissues or organs of a plant are desirable. For example, increased resistance of a plant to infection by soil-borne pathogens might be accomplished by transforming the plant genome with a pathogen-resistance gene such that pathogen-resistance protein is robustly expressed within the roots of the plant. Alternatively, it may be desirable to express a transgene in plant tissues that are in a particular growth or developmental phase such as, for example, cell division or elongation.

Described herein are *Zea mays* Ubi-1 promoter regulatory elements including promoters, upstream-promoters, 5'-UTRs, and introns. Further described are constructs and methods utilizing gene regulatory elements.

SUMMARY

Disclosed herein are promoters, constructs, and methods for expressing a transgene in plant cells, and/or plant tissues. In an embodiment, expression of a transgene comprises use of a promoter. In an embodiment, a promoter comprises a polynucleotide sequence. In an embodiment, a promoter polynucleotide sequence comprises an upstream-promoter, a 5'-untranslated region (5'-UTR) or leader sequence, and an intron. In an embodiment, a promoter polynucleotide sequence comprises the Ubiquitin-1 gene (Ubi-1). In an embodiment, a promoter polynucleotide sequence comprises the Ubi-1 gene of *Zea mays* (*Z. mays*).

In an embodiment, a construct includes a gene expression cassette comprising a promoter polynucleotide sequence that was obtained from the Ubi-1 gene of *Z. mays*. In an embodiment, the Ubi-1 promoter polynucleotide sequence from *Z. mays* comprises an upstream-promoter region, 5'-UTR or leaders sequence, and an intron. In an embodiment, a construct includes a gene expression cassette comprising a promoter polynucleotide sequence obtained from *Z. mays* Ubi-1 gene fused to an intron from the gene encoding Yellow Fluorescent Protein from the *Phialidium* species (PhiYFP). In an embodiment, a construct includes a gene expression cassette comprising a promoter polynucleotide sequence obtained from *Z. mays* Ubi-1 gene fused to an intron from the gene encoding Yellow Fluorescent Protein from the *Phialidium* species (PhiYFP), followed by a 3'-untranslated region (3'-UTR) from the Peroxidase 5 gene of *Z. mays*. (ZmPer5). The resulting polynucleotide sequence comprises a novel promoter gene regulatory element.

In an embodiment, a gene expression cassette includes a gene promoter regulatory element operably linked to a transgene or a heterologous coding sequence. In an embodiment, a gene expression cassette includes at least one, two, three, four, five, six, seven, eight, nine, ten, or more transgenes.

Methods of growing plants expressing a transgene using novel gene promoter regulatory elements (e.g. an upstream-promoter, 5'-UTR, and intron) are disclosed herein. Methods of culturing plant tissues and cells expressing a transgene using the novel gene promoter regulatory element are also disclosed herein. In an embodiment, methods as disclosed herein include constitutive gene expression in plant leaves, roots, calli, and pollen. Methods of purifying a polynucleotide sequence comprising the novel gene promoter regulatory element are also disclosed herein.

BRIEF DESCRIPTION OF THE DRAWINGS

FIG. 3 shows the polynucleotide sequence of *Z. mays* c.v. B73 Ubi-1 control promoter (SEQ ID NO: 1) with the upstream-promoter region underlined, the 5'-UTR/leader sequence shaded, and the intron region in lower case.

FIG. 4 shows the polynucleotide sequence of *Z. mays* c.v. B104 Ubi-1 promoter (SEQ ID NO: 2) with the upstream-promoter region underlined, the 5'-UTR/leader sequence shaded, and the intron region in lower case.

FIG. 5 shows the polynucleotide sequence alignment of the upstream-promoter regions of *Z. mays* c.v. B104 (SEQ ID NO: 4) compared to the *Z. mays* c.v. B73 control upstream-promoter sequence (SEQ ID NO: 3).

FIG. 6 shows the polynucleotide sequence alignment of the 5'-UTR/leader regions of *Z. mays* c.v. B104 (SEQ ID NO: 6) compared to the *Z. mays* c.v. B73 control 5'-UTR/leader sequence (SEQ ID NO: 5).

FIG. 7 shows the polynucleotide sequence alignment of the intron regions of *Z. mays* c.v. B104 (SEQ ID NO: 8) compared to the *Z. mays* c.v. B73 control intron sequence (SEQ ID NO: 7).

DETAILED DESCRIPTION

Definitions

Figure 1:
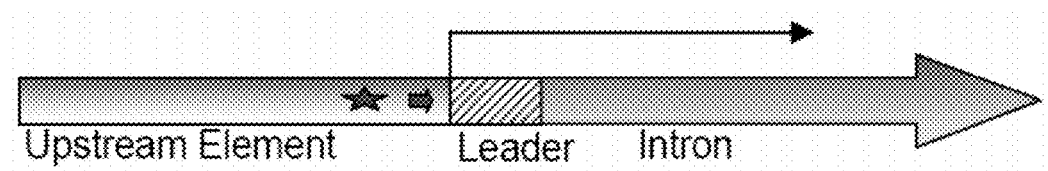
FIG. 1 shows a schematic novel promoter comprising the *Zea mays* c.v. B73 Ubi-1 gene. The promoter is comprised of an upstream element, a 5'-UTR or leader sequence, and an intron. The upstream element is located 5' upstream of the Transcription Start Site (TSS), indicated by the long arrow. The upstream element is comprised of regulatory elements, such as a TATA box, indicated by the short arrow, and a heat shock element, indicated by the star.

As used herein, the articles, "a", "an", and "the" include plural references unless the context clearly and unambiguously dictates otherwise.

As used herein, the term "backcrossing" refers to a process in which a breeder crosses hybrid progeny back to one of the parents, for example, a first generation hybrid F1 with one of the parental genotypes of the F1 hybrid.

As used herein, the term "intron" refers to any nucleic acid sequence comprised in a gene (or expressed nucleotide sequence of interest) that is transcribed but not translated. Introns include untranslated nucleic acid sequence within an expressed sequence of DNA, as well as a corresponding sequence in RNA molecules transcribed therefrom.

A construct described herein may also contain sequences that enhance translation and/or mRNA stability such as introns. An example of one such intron is the first intron of gene II of the histone H3 variant of *Arabidopsis thaliana* or any other commonly known intron sequence. Introns may be used in combination with a promoter sequence to enhance translation and/or mRNA stability.

As used herein, the terms "5'-untranslated region" or "5'-UTR" refers to an untranslated segment in the 5' terminus of pre-mRNAs or mature mRNAs. For example, on mature mRNAs, a 5'-UTR typically harbors on its 5' end a 7-methylguanosine cap and is involved in many processes such as splicing, polyadenylation, mRNA export towards the cytoplasm, identification of the 5' end of the mRNA by the translational machinery, and protection of the mRNAs against degradation.

As used herein, the term "3'-untranslated region" or "3'-UTR" refers to an untranslated segment in a 3' terminus of the pre-mRNAs or mature mRNAs. For example, on mature mRNAs this region harbors the poly-(A) tail and is known to have many roles in mRNA stability, translation initiation, and mRNA export.

As used herein, the term "polyadenylation signal" refers to a nucleic acid sequence present in mRNA transcripts that allows for transcripts, when in the presence of a poly-(A) polymerase, to be polyadenylated on the polyadenylation site, for example, located 10 to 30 bases downstream of the poly-(A) signal. Many polyadenylation signals are known in the art and are useful for the present invention. An exemplary sequence includes AAUAAA and variants thereof, as described in Loke J., et al., (2005) *Plant Physiology* 138(3); 1457-1468.

As used herein, the term "isolated" refers to a biological component (including a nucleic acid or protein) that has been separated from other biological components in the cell of the organism in which the component naturally occurs (i.e., other chromosomal and extra-chromosomal DNA).

As used herein, the term "purified" in reference to nucleic acid molecules does not require absolute purity (such as a homogeneous preparation). Instead, "purified" represents an indication that the sequence is relatively more pure than in its native cellular environment. For example, the "purified" level of nucleic acids should be at least 2-5 fold greater in terms of concentration or gene expression levels as compared to its natural level.

The claimed DNA molecules may be obtained directly from total DNA or from total RNA. In addition, cDNA clones are not naturally occurring, but rather are preferably obtained via manipulation of a partially purified, naturally occurring substance (messenger RNA). The construction of a cDNA library from mRNA involves the creation of a synthetic substance (cDNA). Individual cDNA clones may be purified from the synthetic library by clonal selection of the cells carrying the cDNA library. Thus, the process which includes the construction of a cDNA library from mRNA and purification of distinct cDNA clones yields an approximately $10^6$-fold purification of the native message. Likewise, a promoter DNA sequence may be cloned into a plasmid. Such a clone is not naturally occurring, but rather is preferably obtained via manipulation of a partially purified, naturally occurring substance, such as a genomic DNA library. Thus, purification of at least one order of magnitude, preferably two or three orders, and more preferably four or five orders of magnitude, is favored in these techniques.

Similarly, purification represents an indication that a chemical or functional change in the component DNA sequence has occurred. Nucleic acid molecules and proteins that have been "purified" include nucleic acid molecules and proteins purified by standard purification methods. The term "purified" also embraces nucleic acids and proteins prepared by recombinant DNA methods in a host cell (e.g., plant cells), as well as chemically-synthesized nucleic acid molecules, proteins, and peptides.

The term "recombinant" means a cell or organism in which genetic recombination has occurred. It also includes a molecule (e.g., a vector, plasmid, nucleic acid, polypeptide, or a small RNA) that has been artificially or synthetically (i.e., non-naturally) altered by human intervention. The alteration may be performed on the molecule within, or removed from, its natural environment or state.

As used herein, the term "expression" refers to the process by which a polynucleotide is transcribed into mRNA (including small RNA molecules) and/or the process by which the transcribed mRNA (also referred to as "transcript") is subsequently translated into peptides, polypeptides, or proteins. Gene expression may be influenced by external signals, for example, exposure of a cell, tissue, or organism to an agent that increases or decreases gene expression. Expression of a gene may also be regulated anywhere in the pathway from DNA to RNA to protein. Regulation of gene expression occurs, for example, through controls acting on transcription, translation, RNA transport and processing, degradation of intermediary molecules, such as mRNA, or through activation, inactivation, compartmentalization, or degradation of specific protein molecules after they have been made, or by combinations thereof. Gene expression may be measured at the RNA level or the protein level by any method known in the art, including, without limitation, Northern blot, RT-PCR, Western blot, or in vitro, in situ, or in vivo protein activity assay(s).

As used herein, the terms "homology-based gene silencing" or "HBGS" are generic terms that include both transcriptional gene silencing and post-transcriptional gene silencing. Silencing of a target locus by an unlinked silencing locus may result from transcription inhibition (e.g., transcriptional gene silencing; TGS) or mRNA degradation (e.g., post-transcriptional gene silencing; PTGS), owing to the production of double-stranded RNA (dsRNA) corresponding to promoter or transcribed sequences, respectively. Involvement of distinct cellular components in each process suggests that dsRNA-induced TGS and PTGS likely result from the diversification of an ancient common mechanism. However, a strict comparison of TGS and PTGS has been difficult to achieve, because it generally relies on the analysis of distinct silencing loci. A single transgene locus may be described to trigger both TGS and PTGS, owing to the production of dsRNA corresponding to promoter and transcribed sequences of different target genes.

As used herein, the terms "nucleic acid molecule," "nucleic acid," or "polynucleotide" (all three terms being synonymous with one another) refer to a polymeric form of nucleotides, which may include both sense and anti-sense strands of RNA, cDNA, genomic DNA, and synthetic forms, and mixed polymers thereof. A "nucleotide" may refer to a ribonucleotide, deoxyribonucleotide, or a modified form of either type of nucleotide. A nucleic acid molecule is usually at least ten bases in length, unless otherwise specified. The terms may refer to a molecule of RNA or DNA of indeterminate length. The terms include single- and double-stranded forms of DNA. A nucleic acid molecule may include either or both naturally-occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of ordinary skill in the art. Such modifications include, for example, labels, methylation, substitution of one or more of the naturally-occurring nucleotides with an analog, internucleotide modifications (e.g., uncharged linkages, such as, methyl phosphonates, phosphotriesters, phosphoramidates, carbamates, etc.; charged linkages, such as, phosphorothioates, phosphorodithioates, etc.; pendent moieties, such as, peptides; intercalators, such as, acridine, psoralen, etc.; chelators; alkylators; and modified linkages, such as, alpha anomeric nucleic acids, etc.). The term "nucleic acid molecule" also includes any topological conformation, including single-stranded, double-stranded, partially duplexed, triplexed, hairpinned, circular, and padlocked conformations.

Transcription proceeds in a 5' to 3' manner along a DNA strand. This means that RNA is made by sequential addition of ribonucleotide-5'-triphosphates to the 3' terminus of the growing chain with a requisite elimination of the pyrophosphate. In either a linear or circular nucleic acid molecule, discrete elements (e.g., particular nucleotide sequences) may be referred to as being "upstream" relative to a further element if they are bonded or would be bonded to the same nucleic acid in the 5' direction from that element. Similarly, discrete elements may be referred to as being "downstream" relative to a further element if they are or would be bonded to the same nucleic acid in the 3' direction from that element.

As used herein, the term "base position" refers to the location of a given base or nucleotide residue within a designated nucleic acid. A designated nucleic acid may be defined by alignment with a reference nucleic acid.

As used herein, the term "hybridization" refers to a process where oligonucleotides and their analogs hybridize by hydrogen bonding, which includes Watson-Crick, Hoogsteen, or reversed Hoogsteen hydrogen bonding, between complementary bases. Generally, nucleic acid molecules consist of nitrogenous bases that are either pyrimidines, such as cytosine (C), uracil (U), and thymine (T), or purines, such as adenine (A) and guanine (G). Nitrogenous bases form hydrogen bonds between a pyrimidine and a purine, and bonding of a pyrimidine to a purine is referred to as "base pairing." More specifically, A will form a specific hydrogen bond to T or U, and G will specifically bond to C. "Complementary" refers to the base pairing that occurs between two distinct nucleic acid sequences or two distinct regions of the same nucleic acid sequence.

As used herein, the terms "specifically hybridizable" and "specifically complementary" refer to a sufficient degree of complementarity such that stable and specific binding occurs between an oligonucleotide and a DNA or RNA target. Oligonucleotides need not be 100% complementary to the target sequence to specifically hybridize. An oligonucleotide is specifically hybridizable when binding of the oligonucleotide to the target DNA or RNA molecule interferes with the normal function of the target DNA or RNA, and there is sufficient degree of complementarity to avoid non-specific binding of an oligonucleotide to non-target sequences under conditions where specific binding is desired, for example, under physiological conditions in the case of in vivo assays or systems. Such binding is referred to as specific hybridization. Hybridization conditions resulting in particular degrees of stringency will vary depending upon the nature of the chosen hybridization method and the composition and length of the hybridizing nucleic acid sequences. Generally, the temperature of hybridization and the ionic strength (especially $Na^+$ and/or $Mg^{2+}$ concentration) of a hybridization buffer will contribute to the stringency of hybridization, though wash times also influence stringency. Calculations regarding hybridization conditions required for attaining particular degrees of stringency are discussed in Sambrook et al. (ed.), Molecular Cloning: A Laboratory Manual, 2nd ed., vol. 1-3, Cold Spring Harbor Laboratory Press, Cold Spring Harbor, N.Y., 1989.

As used herein, the term "stringent conditions" encompasses conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize.

In particular embodiments, stringent conditions can include hybridization at 65° C., followed by washes at 65° C. with 0.1×SSC/0.1% SDS for 40 minutes. The following are representative, non-limiting hybridization conditions:

Very High Stringency: Hybridization in 5×SSC buffer at 65° C. for 16 hours; wash twice in 2×SSC buffer at room temperature for 15 minutes each; and wash twice in 0.5×SSC buffer at 65° C. for 20 minutes each.

High Stringency: Hybridization in 5-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Moderate Stringency: Hybridization in 6×SSC buffer at room temperature to 55° C. for 16-20 hours; wash at least twice in 2-3×SSC buffer at room temperature to 55° C. for 20-30 minutes each.

In an embodiment, specifically hybridizable nucleic acid molecules may remain bound under very high stringency hybridization conditions. In an embodiment, specifically hybridizable nucleic acid molecules may remain bound under high stringency hybridization conditions. In an embodiment, specifically hybridizable nucleic acid molecules may remain bound under moderate stringency hybridization conditions.

As used herein, the term "oligonucleotide" refers to a short nucleic acid polymer. Oligonucleotides may be formed by cleavage of longer nucleic acid segments or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in Polymerase Chain Reaction, a technique for the amplification of small DNA sequences. In Polymerase Chain Reaction, an oligonucleotide is typically referred to as a "primer" which allows a DNA polymerase to extend the oligonucleotide and replicate the complementary strand.

As used herein, the terms "Polymerase Chain Reaction" or "PCR" refer to a procedure or technique in which minute amounts of nucleic acid, RNA, and/or DNA, are amplified as described in U.S. Pat. No. 4,683,195. Generally, sequence information from the ends of the region of interest or beyond needs to be available, such that oligonucleotide primers may be designed. PCR primers will be identical or similar in sequence to opposite strands of the nucleic acid template to be amplified. The 5' terminal nucleotides of the two primers may coincide with the ends of the amplified material. PCR may be used to amplify specific RNA sequences or DNA sequences from total genomic DNA and cDNA transcribed from total cellular RNA, bacteriophage, or plasmid sequences, etc. See generally Mullis et al., *Cold Spring Harbor Symp. Quant. Biol.*, 51:263 (1987); Erlich, ed., PCR Technology, (Stockton Press, NY, 1989).

As used herein, the term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates (i.e., A, T, G, and C) and at least one polymerization-inducing agent or enzyme such as Reverse Transcriptase or DNA polymerase. These reagents are typically present in a suitable buffer that may include constituents which are co-factors or which affect conditions, such as pH and the like at various suitable temperatures. A primer is preferably a single strand sequence, such that amplification efficiency is optimized, but double stranded sequences may be utilized.

As used herein, the term "probe" refers to an oligonucleotide or polynucleotide sequence that hybridizes to a target sequence. In the TaqMan® or TaqMan®-style assay procedure, the probe hybridizes to a portion of the target situated between the annealing site of the two primers. A probe includes about eight nucleotides, about ten nucleotides, about fifteen nucleotides, about twenty nucleotides, about thirty nucleotides, about forty nucleotides, or about fifty nucleotides. In some embodiments, a probe includes from about eight nucleotides to about fifteen nucleotides.

In the Southern blot assay procedure, the probe hybridizes to a DNA fragment that is attached to a membrane. A probe includes about ten nucleotides, about 100 nucleotides, about 250 nucleotides, about 500 nucleotides, about 1,000 nucleotides, about 2,500 nucleotides, or about 5,000 nucleotides. In some embodiments, a probe includes from about 500 nucleotides to about 2,500 nucleotides.

A probe may further include a detectable label, such as, a radioactive label, a biotinylated label, a fluorophore (e.g., Texas-Red®, fluorescein isothiocyanate, etc.,). The detectable label may be covalently attached directly to the probe oligonucleotide, such that the label is located at the 5' end or 3' end of the probe. A probe comprising a fluorophore may also further include a quencher dye (e.g., Black Hole Quencher™, Iowa Black™, etc.).

As used herein, the terms "sequence identity" or "identity" may be used interchangeably and refer to nucleic acid residues in two sequences that are the same when aligned for maximum correspondence over a specified comparison window.

As used herein, the term "percentage of sequence identity" or "percentage of sequence homology" refers to a value determined by comparing two optimally aligned sequences (e.g., nucleic acid sequences or amino acid sequences) over a comparison window, wherein the portion of a sequence in the comparison window may comprise additions, substitutions, mismatches, and/or deletions (i.e., gaps) as compared to a reference sequence in order to obtain optimal alignment of the two sequences. A percentage is calculated by determining the number of positions at which an identical nucleic acid or amino acid residue occurs in both sequences to yield the number of matched positions, dividing the number of matched positions by the total number of positions in the comparison window, and multiplying the result by 100 to yield the percentage of sequence identity. Methods for aligning sequences for comparison are well known. Various bioinformatics or computer programs and alignment algorithms, such as ClustalW and Sequencher, are also well known in the art and/or described in, for example: Smith and Waterman (1981) *Adv. Appl. Math.* 2:482; Needleman and Wunsch (1970) *J. Mol. Biol.* 48:443; Pearson and Lipman (1988) *Proc. Natl. Acad. Sci. U.S.A.* 85:2444; Higgins and Sharp (1988) *Gene* 73:237-44; Higgins and Sharp (1989) *CABIOS* 5:151-3; Corpet et al. (1988) *Nucleic Acids Res.* 16:10881-90; Huang et al. (1992) *Comp. Appl. Biosci.* 8:155-65; Pearson et al. (1994) *Methods Mol. Biol.* 24:307-31; Tatiana et al. (1999) *FEMS Microbiol. Lett.* 174:247-50.

The National Center for Biotechnology Information (NCBI) Basic Local Alignment Search Tool (BLAST™; Altschul et al. (1990) *J. Mol. Biol.* 215:403-10) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method.

As used herein, the term "operably linked" refers to a nucleic acid placed into a functional relationship with another nucleic acid. Generally, "operably linked" may mean that linked nucleic acids are contiguous. Linking may be accomplished by ligation at convenient restriction sites. If such sites do not exist, synthetic oligonucleotide adaptors or linkers are ligated or annealed to the nucleic acid and used to link the contiguous polynucleotide fragment. However, elements need not be contiguous to be operably linked.

As used herein, the term "promoter" refers to a region of DNA that is generally located upstream of a gene (i.e., towards the 5' end of a gene) and is necessary to initiate and drive transcription of the gene. A promoter may permit proper activation or repression of a gene that it controls. A promoter may contain specific sequences that are recognized by transcription factors. These factors may bind to a promoter DNA sequence, which results in the recruitment of RNA polymerase, an enzyme that synthesizes RNA from the coding region of the gene. The promoter generally refers to all gene regulatory elements located upstream of the gene, including, 5'-UTR, introns, and leader sequences.

As used herein, the term "upstream-promoter" refers to a contiguous polynucleotide sequence that is sufficient to direct initiation of transcription. As used herein, an upstream-promoter encompasses the site of initiation of transcription with several sequence motifs, which include a TATA Box, initiator (Intr) sequence, TFIIB recognition elements (BRE), and other promoter motifs (Jennifer, E. F. et al, (2002) *Genes & Dev.*, 16: 2583-2592). The upstream-promoter provides the site of action to RNA polymerase II, a multi-subunit enzyme with the basal or general transcription factors like, TFIIA, B, D, E, F, and H. These factors assemble into a transcription pre-initiation complex (PIC) that catalyzes the synthesis of RNA from a DNA template.

The activation of the upstream-promoter is performed by the addition of regulatory DNA sequence elements to which various proteins bind and subsequently interact with the transcription initiation complex to activate gene expression. These gene regulatory element sequences interact with specific DNA-binding factors. These sequence motifs may sometimes be referred to as cis-elements. Such cis-elements, to which tissue-specific or development-specific transcription factors bind, individually or in combination, may determine the spatiotemporal expression pattern of a promoter at the transcriptional level. These cis-elements vary widely in the type of control they exert on operably linked genes. Some elements act to increase the transcription of operably-linked genes in response to environmental responses (e.g., temperature, moisture, and wounding). Other cis-elements may respond to developmental cues (e.g., germination, seed maturation, and flowering) or to spatial information (e.g., tissue specificity). See, for example, Langridge et al. (1989) Proc. Natl. Acad. Sci. USA 86:3219-23. These cis-elements are located at a varying distance from the transcription start point. Some cis-elements (called proximal elements) are adjacent to a minimal core promoter region, while other elements may be positioned several kilobases 5' upstream or 3' downstream of the promoter (enhancers).

As used herein, the term "transformation" encompasses all techniques in which a nucleic acid molecule may be introduced into a cell. Examples include, but are not limited to: transfection with viral vectors; transformation with plasmid vectors; electroporation; lipofection; microinjection (Mueller et al. (1978) Cell 15:579-85); *Agrobacterium*-mediated transfer; direct DNA uptake; WHISKERS™-mediated transformation; and microprojectile bombardment. These techniques may be used for both stable transformation and transient transformation of a plant cell. "Stable transformation" refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms. "Transient transformation" refers to the introduction of a nucleic acid fragment into the nucleus or DNA-containing organelle of a host organism, resulting in gene expression without genetically stable inheritance.

As used herein, the term "transduce" refers to a process where a virus transfers nucleic acid into a cell.

As used herein, the term "transgene" refers to an exogenous nucleic acid sequence. In one example, a transgene is a gene sequence (e.g., an herbicide-resistance gene), a gene encoding an industrially or pharmaceutically useful compound, or a gene encoding a desirable agricultural trait. In yet another example, a transgene is an antisense nucleic acid sequence, wherein expression of the antisense nucleic acid sequence inhibits expression of a target nucleic acid sequence. A transgene may contain regulatory sequences operably linked to the transgene (e.g., a promoter, intron, 5'-UTR, or 3'-UTR). In some embodiments, a nucleic acid of interest is a transgene. However, in other embodiments, a nucleic acid of interest is an endogenous nucleic acid, wherein additional genomic copies of the endogenous nucleic acid are desired, or a nucleic acid that is in the antisense orientation with respect to the sequence of a target nucleic acid in a host organism.

As used herein, the term "vector" refers to a nucleic acid molecule as introduced into a cell, thereby producing a transformed cell. A vector may include nucleic acid sequences that permit it to replicate in the host cell, such as an origin of replication. Examples include, but are not limited to, a plasmid, cosmid, bacteriophage, bacterial artificial chromosome (BAC), or virus that carries exogenous DNA into a cell. A vector may also include one or more genes, antisense molecules, selectable marker genes, and other genetic elements known in the art. A vector may transduce, transform, or infect a cell, thereby causing the cell to express the nucleic acid molecules and/or proteins encoded by the vector. A vector may optionally include materials to aid in achieving entry of the nucleic acid molecule into the cell (e.g., a liposome).

As used herein, the terms "cassette," "expression cassette," and "gene expression cassette" refer to a segment of DNA that may be inserted into a nucleic acid or polynucleotide at specific restriction sites or by homologous recombination. A segment of DNA comprises a polynucleotide containing a gene of interest that encodes a small RNA or a polypeptide of interest, and the cassette and restriction sites are designed to ensure insertion of the cassette in the proper reading frame for transcription and translation. In an embodiment, an expression cassette may include a polynucleotide that encodes a small RNA or a polypeptide of interest and may have elements in addition to the polynucleotide that facilitate transformation of a particular host cell. In an embodiment, a gene expression cassette may also include elements that allow for enhanced expression of a small RNA or a polynucleotide encoding a polypeptide of interest in a host cell. These elements may include, but are not limited to: a promoter, a minimal promoter, an enhancer, a response element, an intron, a 5'-UTR, a 3'-UTR, a terminator sequence, a polyadenylation sequence, and the like.

As used herein, the term "heterologous coding sequence" is used to indicate any polynucleotide that codes for, or ultimately codes for, a peptide or protein or its equivalent amino acid sequence, e.g., an enzyme, that is not normally present in the host organism and may be expressed in the host cell under proper conditions. As such, "heterologous coding sequences" may include one or additional copies of coding sequences that are not normally present in the host cell, such that the cell is expressing additional copies of a coding sequence that are not normally present in the cells. The heterologous coding sequences may be RNA or any type thereof (e.g., mRNA), DNA or any type thereof (e.g., cDNA), or a hybrid of RNA/DNA. Examples of coding sequences include, but are not limited to, full-length transcription units that comprise such features as the coding sequence, introns, promoter regions, 5'-UTR, 3'-UTR, and enhancer regions.

"Heterologous coding sequences" also include the coding portion of the peptide or enzyme (i.e., the cDNA or mRNA sequence), the coding portion of the full-length transcriptional unit (i.e., the gene comprising introns and exons), "codon optimized" sequences, truncated sequences or other forms of altered sequences that code for the enzyme or code for its equivalent amino acid sequence, provided that the equivalent amino acid sequence produces a functional protein. Such equivalent amino acid sequences may have a deletion of one or more amino acids, with the deletion being N-terminal, C-terminal, or internal. Truncated forms are envisioned as long as they have the catalytic capability indicated herein.

As used herein, the term "control" refers to a sample used in an analytical procedure for comparison purposes. A control can be "positive" or "negative". For example, where the purpose of an analytical procedure is to detect a differentially expressed transcript or polypeptide in cells or tissue, it is generally preferable to include a positive control, such as a sample from a known plant exhibiting the desired expression, and a negative control, such as a sample from a known plant lacking the desired expression.

As used herein, the term "plant" includes plants and plant parts including, but not limited to, plant cells and plant tissues, such as leaves, calli, stems, roots, flowers, pollen, and seeds. A class of plants that may be used in the present invention is generally as broad as the class of higher and lower plants amenable to mutagenesis including angiosperms, gymnosperms, ferns, and multicellular algae. Thus, "plant" includes dicot and monocot plants. Examples of dicotyledonous plants include tobacco, Arabidopsis, soybean, tomato, papaya, canola, sunflower, cotton, alfalfa, potato, grapevine, pigeon pea, pea, Brassica, chickpea, sugar beet, rapeseed, watermelon, melon, pepper, peanut, pumpkin, radish, spinach, squash, broccoli, cabbage, carrot, cauliflower, celery, Chinese cabbage, cucumber, eggplant, and lettuce. Examples of monocotyledonous plants include corn, rice, wheat, sugarcane, barley, rye, sorghum, orchids, bamboo, banana, cattails, lilies, oat, onion, millet, and triticale.

As used herein, the term "plant material" refers to leaves, calli, stems, roots, flowers or flower parts, fruits, pollen, egg cells, zygotes, seeds, cuttings, cell or tissue cultures, or any other part or product of a plant. In an embodiment, plant material includes cotyledon and leaf. In an embodiment, plant material includes root tissues and other plant tissues located underground.

As used herein, the term "selectable marker gene" refers to a gene that is optionally used in plant transformation to, for example, protect plant cells from a selective agent or provide resistance/tolerance to a selective agent. In addition, "selectable marker gene" is meant to encompass reporter genes. Only those cells or plants that receive a functional selectable marker are capable of dividing or growing under conditions having a selective agent. Examples of selective agents may include, for example, antibiotics, including spectinomycin, neomycin, kanamycin, paromomycin, gentamicin, and hygromycin. These selectable markers include neomycin phosphotransferase (npt II), which expresses an enzyme conferring resistance to the antibiotic kanamycin, and genes for the related antibiotics neomycin, paromomycin, gentamicin, and G418, or the gene for hygromycin phosphotransferase (hpt), which expresses an enzyme conferring resistance to hygromycin. Other selectable marker genes may include genes encoding herbicide resistance including bar or pat (resistance against glufosinate ammonium or phosphinothricin), acetolactate synthase (ALS, resistance against inhibitors such as sulfonylureas (SUs), imidazolinones (IMIs), triazolopyrimidines (TPs), pyrimidinyl oxybenzoates (POBs), and sulfonylamino carbonyl triazolinones that prevent the first step in the synthesis of the branched-chain amino acids), glyphosate, 2,4-D, and metal resistance or sensitivity. Examples of "reporter genes" that may be used as a selectable marker gene include the visual observation of expressed reporter gene proteins, such as proteins encoding β-glucuronidase (GUS), luciferase, green fluorescent protein (GFP), yellow fluorescent protein (YFP), DsRed, β-galactosidase, chloramphenicol acetyltransferase (CAT), alkaline phosphatase, and the like. The phrase "marker-positive" refers to plants that have been transformed to include a selectable marker gene.

As used herein, the term "detectable marker" refers to a label capable of detection, such as, for example, a radioisotope, fluorescent compound, bioluminescent compound, a chemiluminescent compound, metal chelator, or enzyme. Examples of detectable markers include, but are not limited to, the following: fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In an embodiment, a detectable marker may be attached by spacer arms of various lengths to reduce potential steric hindrance.

As used herein, the term "detecting" is used in the broadest sense to include both qualitative and quantitative measurements of a specific molecule, for example, measurements of a specific polypeptide.

Unless otherwise specifically explained, all technical and scientific terms used herein have the same meaning as commonly understood by those of ordinary skill in the art that this disclosure belongs. Definitions of common terms in molecular biology maybe found in, for example: Lewin, Genes V, Oxford University Press, 1994; Kendrew et al. (eds.), The Encyclopedia of Molecular Biology, Blackwell Science Ltd., 1994; and Meyers (ed.), Molecular Biology and Biotechnology: A Comprehensive Desk Reference, VCH Publishers, Inc., 1995.

Promoters as Gene Expression Regulatory Elements

Plant promoters used for basic research or biotechnological applications are generally unidirectional, directing the constitutive expression of a transgene that has been fused to its 3' end (downstream). It is often necessary to robustly express transgenes within plants for metabolic engineering and trait stacking. In addition, multiple novel promoters are typically required in transgenic crops to drive the expression of multiple genes. Disclosed herein is a constitutive promoter that can direct the expression of a transgene that has been fused at its 3' end.

Development of transgenic products is becoming increasingly complex, which requires robustly expressing transgenes and stacking multiple transgenes into a single locus. Traditionally, each transgene requires a unique promoter for expression wherein multiple promoters are required to express different transgenes within one gene stack. With an increasing size of gene stacks, this method frequently leads to repeated use of the same promoter to obtain similar levels of expression patterns of different transgenes for expression of a single polygenic trait.

Multi-gene constructs driven by the same promoter are known to cause gene silencing resulting in less efficacious transgenic products in the field. Excess of transcription factor (TF)-binding sites due to promoter repetition can cause depletion of endogenous TFs leading to transcriptional inactivation. The silencing of transgenes is likely to undesirably affect performance of a transgenic plant produced to express transgenes. Repetitive sequences within a transgene may lead to gene intra locus homologous recombination resulting in polynucleotide rearrangements.

In addition to constitutive promoters, tissue-specific, or organ-specific promoters drive gene expression in certain tissues such as in the kernel, root, leaf, callus, pollen, or tapetum of the plant. Tissue and developmental-stage specific promoters drive the expression of genes, which are expressed in particular tissues or at particular time periods during plant development. Tissue-specific promoters are required for certain applications in the transgenic plant industry and are desirable as they permit specific expression of heterologous genes in a tissue and/or in a selected developmental stages, indicating expression of the heterologous gene differentially in various organs, tissues, and/or at different times, but not others.

For example, increased resistance of a plant to infection by soil-borne pathogens might be accomplished by transforming the plant genome with a pathogen-resistance gene such that a pathogen-resistance protein is robustly expressed within the plant. Alternatively, it may be desirable to express a transgene in plant tissues that are in a particular growth or developmental phase such as, for example, cell division or elongation. Another application is the desirability of using tissue-specific promoters, such that the promoters would confine the expression of the transgenes encoding an agronomic trait in developing plant parts (i.e., roots, leaves, calli, or pollen).

The promoters described herein are promising tools for making commercial transgene constructs containing multiple genes. These promoters also provide structural stability in bacterial hosts and functional stability in plant cells, such as reducing transgene silencing, to enable transgene expression. Promoters with varying expression ranges may also be obtained by employing the methods described herein. Compared to transgene constructs using a single promoter multiple times, the diversified promoter constructs described in this application are more compatible for downstream molecular analyses of transgenic events. Use of the diversified promoters described herein may also alleviate rearrangements in transgenic multigene loci during targeting with zinc finger technology (SHUKLA et al. 2009).

Zea mays Ubiquitin-1 Promoters

The Zea mays Ubi-1 promoter has been a biotech industry standard, predominantly used for stable, high transgenic expression in maize (CHRISTENSEN and QUAIL 1996; CHRISTENSEN et al. 1992; TOKI et al. 1992). Each transgene usually requires a specific promoter for sufficient expression. Multiple promoters are typically required to express different transgenes within one gene stack. This paradigm frequently leads to the repetitive use of the Z. mays Ubi-1 promoter due to its desired high levels of protein expression and constitutive expression pattern.

However, the deliberate introduction of repetitive sequences into a transgenic locus can also lead to undesirable negative effects on transgene expression and stability (FLADUNG and KUMAR 2002; KUMAR and FLADUNG 2000a; KUMAR and FLADUNG 2000b; KUMAR and FLADUNG 2001a; KUMAR and FLADUNG 2001b; KUMAR and FLADUNG 2002; METTE et al. 1999; MOURRAIN et al. 2007). The challenge of multiple coordinated transgene expression may be addressed using a promoter diversity approach, where different promoters are used to drive different transgenes with the same expression profile (PEREMARTI et al. 2010). This application describes a diversified Ubi-1 promoter sequence obtained by identifying and purifying the novel promoter from different Zea mays genotypes.

Transcription initiation and modulation of gene expression in plant genes is directed by a variety of DNA sequence elements collectively arranged in a larger sequence called a promoter. Eukaryotic promoters typically consist of a minimal core promoter and upstream regulatory sequences. The core promoter is a minimal stretch of contiguous DNA sequence that is sufficient to direct accurate initiation of transcription. Core promoters in plants generally comprise canonical regions associated with the initiation of transcription, such as CAAT and TATA boxes (consensus sequence TATAWAW). The TATA box element is usually located approximately 20 to 35 base pairs (bp) upstream of the transcription start site (TSS). The activation of the core promoter is accomplished by upstream regulatory sequences to which various proteins bind and subsequently interact with the transcription initiation complex to activate gene expression. These regulatory elements comprise DNA sequences which determine the spatio-temporal expression pattern of a promoter.

Referring to FIG. 1, the Z. mays Ubi-1 gene promoter is derived from the Z. mays inbred cell line B73. The Z. mays Ubi-1 promoter is comprised of approximately 895 bp of DNA sequence located 5' upstream of the TSS (i.e., the Upstream Element). In addition, the Z. mays Ubi-1 promoter is comprised of about 1093 bp of DNA sequence located 3' downstream of the TSS (see U.S. Pat. No. 5,510,474). Thus, the Z. mays Ubi-1 promoter is comprised of approximately 2 Kilo base pairs (kb) of total DNA sequence.

The Upstream Element of the Z. mays Ubi-1 promoter comprises a TATA box located approximately 30 bp 5' upstream of the TSS (FIGS. 1 and 3). In addition, the Upstream Element comprises two overlapping heat shock consensus elements located immediately 5' upstream of the TSS. An 82 bp 5'-UTR or leader sequence is located immediately 3' downstream of the TSS and is followed by an intron that extends from base 83 to 1093 (FIGS. 1 and 3).

Previous work has described increased gene expression of genes and/or transgenes regulated by the Z. mays Ubi-1 promoter. For example, the transcription fusion of the Chloramphenicol Acetyltransferase (CAT) gene to the Z. mays Ubi-1 promoter yielded more than 10-fold higher level of CAT activity in maize protoplasts than expression driven by the Cauliflower Mosaic Virus 35S promoter (CHRISTENSEN and QUAIL 1996; CHRISTENSEN et al. 1992).

In addition to the control Z. mays Ubi-1 promoter, this application describes a novel maize Ubi-1 promoter. Unlike the control Ubi-1 promoter derived from Z. mays genotype c.v. B73, the novel Ubi-1 promoter was derived from *Z. mays* genotype c.v. B104. Provided are constructs and methods using a *Z. mays* Ubi-1 promoter comprising a polynucleotide sequence. In an embodiment, a promoter may comprise a polynucleotide sequence from *Z. mays* c.v. B73 Ubi-1 gene as follows:

(SEQ ID NO: 1)
```
GTGCAGCGTGACCCGGTCGTGCCCCTCTCTAGAGATAATGAGCATTGCATGTC
TAAGTTATAAAAAATTACCACATATTTTTTTGTCACACTTGTTTGAAGTGCAGTTTA
TCTATCTTTATACATATATTTAAACTTTACTCTACGAATAATATAATCTATAGTACTA
CAATAATATCAGTGTTTTAGAGAATCATATAAATGAACAGTTAGACATGGTCTAAAG
GACAATTGAGTATTTTGACAACAGGACTCTACAGTTTTATCTTTTTAGTGTGCATGTG
TTCTCCTTTTTTTTGCAAATAGCTTCACCTATATAATACTTCATCCATTTTATTAGTA
CATCCATTTAGGGTTTAGGGTTAATGGTTTTTATAGACTAATTTTTTAGTACATCTA
TTTTATTCTATTTTAGCCTCTAAATTAAGAAAACTAAAACTCTATTTTAGTTTTTTTAT
TTAATAGTTTAGATATAAAATAGAATAAAATAAAGTGACTAAAAATTAAACAAATA
CCCTTTAAGAAATTAAAAAAACTAAGGAAACATTTTTCTTGTTTCGAGTAGATAATG
CCAGCCTGTTAAACGCCGTCGACGAGTCTAACGGACACCAACCAGCGAACCAGCAG
CGTCGCGTCGGGCCAAGCGAAGCAGACGGCACGGCATCTCTGTCGCTGCCTCTGGA
CCCCTCTCGAGAGTTCCGCTCCACCGTTGGACTTGCTCCGCTGTCGGCATCCAGAAA
TTGCGTGGCGGAGCGGCAGACGTGAGCCGGCACGGCAGGCGGCCTCCTCCTCCTCT
CACGGCACCGGCAGCTACGGGGATTCCTTTCCCACCGCTCCTTCGCTTTCCCTTCCT
CGCCCGCCGTAATAAATAGACACCCCCTCCACACCCTCTTTCCCCAACCTCGTGTTG
TTCGGAGCGCACACACACACAACCAGATCTCCCCCAAATCCACCCGTCGGCACCTCC
GCTTCAAGGTACGCCGCTCGTCCTCCCCCCCCCCCCCCCTCTCTACCTTCTCTAGATC
GGCGTTCCGGTCCATGCATGGTTAGGGCCCGGTAGTTCTACTTCTGTTCATGTTTGTG
TTAGATCCGTGTTTGTGTTAGATCCGTGCTGCTAGCGTTCGTACACGGATGCGACCT
GTACGTCAGACACGTTCTGATTGCTAACTTGCCAGTGTTTCTCTTTGGGGAATCCTGG
GATGGCTCTAGCCGTTCCGCAGACGGGATCGATTTCATGATTTTTTTGTTTCGTTGC
ATAGGGTTTGGTTTGCCCTTTTCCTTTATTTCAATATATGCCGTGCACTTGTTTGTCGG
GTCATCTTTTCATGCTTTTTTTGTCTTGGTTGTGATGATGTGGTCTGGTTGGGCGGTC
GTTCTAGATCGGAGTAGAATTCTGTTTCAAACTACCTGGTGGATTTATTAATTTTGGA
TCTGTATGTGTGTGCCATACATATTCATAGTTACGAATTGAAGATGATGGATGGAAA
TATCGATCTAGGATAGGTATACATGTTGATGCGGGTTTTACTGATGCATATACAGAG
ATGCTTTTTGTTCGCTTGGTTGTGATGATGTGGTGTGGTTGGGCGGTCGTTCATTCGT
TCTAGATCGGAGTAGAATACTGTTTCAAACTACCTGGTGTATTTATTAATTTTGGAAC
TGTATGTGTGTCATACATCTTCATAGTTACGAGTTTAAGATGGATGGAAATATCG
ATCTAGGATAGGTATACATGTTGATGTGGGTTTTACTGATGCATATACATGATGGCA
TATGCAGCATCTATTCATATGCTCTAACCTTGAGTACCTATCTATTATAATAAACAAG
TATGTTTTATAATTATTTCGATCTTGATATACTTGGATGATGGCATATGCAGCAGCTA
TATGTGGATTTTTTAGCCCTGCCTTCATACGCTATTTATTTGCTTGGTACTGTTTCTT
TTGTCGATGCTCACCCTGTTGTTTGGTGTTACTTCTGCA
```

In another embodiment, a promoter may comprise a polynucleotide sequence from Z. mays c.v. B104 Ubi-1 gene as follows:

(SEQ ID NO: 2)
GACCCGGTCGTGCCCCTCTCTAGAGATAATGAGCATTGCATGTCTAAGTTATA
AAAAATTACCACATATTTTTTTGTCACACTTGTTTGAAGTGCAGTTTATCTATCTTT
ATACATATATTTAAACTTTACTCTACGAATAATATAATCTATAGTACTACAATAATAT
CAGTGTTTTAGAGAATCATATAAATGAACAGTTAGACATGGTCTAAAGGACAATTG
AGTATTTTGACAACAGGACTCTACAGTTTTATCTTTTTAGTGTGCATGTGTTCTCCTT
TTTTTTTGCAAATAGCTTCACCTATATAATACTTCATCCATTTTATTAGTACATCCATT
TAGGGTTTAGGGTTAATGGTTTTTATAGACTAATTTTTTTAGTACATCTATTTTATTCT
ATTTTAGCCTCTAAATTAAGAAAACTAAAACTCTATTTTAGTTTTTTTATTTAATAAT
TTAGATATAAAATAGAATAAAATAAAGTGACTAAAAATTAAACAAATACCCTTTAA
GAAATTAAAAAAACTAAGGAAACATTTTTCTTGTTTCGAGTAGATAATGCCAGCCTG
TTAAACGCCGTCGACGAGTCTAACGGACACCAACCAGCGAACCAGCAGCGTCGCGT
CGGGCCAAGCGAAGCAGACGGCACGGCATCTCTGTCGCTGCCTCTGGACCCCTCTCG
AGAGTTCCGCTCCACCGTTGGACTTGCTCCGCTGTCGGCATCCAGAAATTGCGTGGC
GGAGCGGCAGACGTGAGCCGGCACGGCAGGCGGCCTCCTCCTCCTCTCACGGCACC
GGCAGCTACGGGGGATTCCTTTCCCACCGCTCCTTCGCTTTCCCTTCCTCGCCCGCCG
TAATAAATAGACACCCCCTCCACACCCTCTTTCCCCAACCTCGTGTTGTTCGGAGCG
CACACACACACAACCAGATCTCCCCCAAATCCACCCGTCGGCACCTCCGCTTCAAGG
TACGCCGCTCGTCCTCCCCCCCCCCCTCTCTACCTTCTCTAGATCGGCGTTCCGGTCC
ATGGTTAGGGCCCGGTAGTTCTACTTCTGTTCATGTTTGTGTTAGATCCGTGTTTGTG
TTAGATCCGTGCTGCTAGCGTTCGTACACGGATGCGACCTGTACGTCAGACACGTTC
TGATTGCTAACTTGCCAGTGTTTCTCTTTGGGGAATCCTGGGATGGCTCTAGCCGTTC
CGCAGACGGGATCGATTTCATGATTTTTTTGTTTCGTTGCATAGGGTTTGGTTTGCC
CTTTTCCTTTATTTCAATATATGCCGTGCACTTGTTTGTCGGGTCATCTTTTCATGCTT
TTTTTTGTCTTGGTTGTGATGATGTGGTCTGGTTGGGCGGTCGTTCTAGATCGGAGTA
GAATTCTGTTTCAAACTACCTGGTGGATTTATTAATTTTGGATCTGTATGTGTGTGCC
ATACATATTCATAGTTACGAATTGAAGATGATGGATGGAAATATCGATCTAGGATAG
GTATACATGTTGATGCGGGTTTTACTGATGCATATACAGAGATGCTTTTTGTTCGCTT
GGTTGTGATGATGTGGTGTGGTTGGGCGGTCGTTCATTCGTTCTAGATCGGAGTAGA
ATACTGTTTCAAACTACCTGGTGTATTTATTAATTTTGGAACTGTATGTGTGTGTCAT
ACATCTTCATAGTTACGAGTTTAAGATGGATGGAAATATCGATCTAGGATAGGTATA
CATGTTGATGTGGGTTTTACTGATGCATATACATGATGGCATATGCAGCATCTATTC
ATATGCTCTAACCTTGAGTACCTATCTATTATAATAAACAAGTATGTTTTATAATTAT
TTTGATCTTGATATACTTGGATGATGGCATATGCAGCAGCTATATGTGGATTTTTTA
GCCCTGCCTTCATACGCTATTTATTTGCTTGGTACTGTTTCTTTTGTCGATGCTCACCC
TGTTGTTTGGTGTTACTTCTGCAG

The promoters described herein were characterized by cloning and subsequent DNA sequence homology analysis to identify specific regions of the promoter (i.e., the upstream-promoter, 5'-UTR, and intron regions). Provided are constructs and methods using a constitutive *Z. mays* Ubi-1 promoter comprising polynucleotide sequences of an upstream-promoter region, 5-UTR or leader region, and an intron to express transgenes in plants. In an embodiment, a promoter may comprise an upstream-promoter polynucleotide sequence from *Z. mays* c.v. B73 Ubi-1 gene as follows:

```
                                                     (SEQ ID NO: 3)
GTGCAGCGTGACCCGGTCGTGCCCCTCTCTAGAGATAATGAGCATTGCATGTC

TAAGTTATAAAAAATTACCACATATTTTTTTGTCACACTTGTTTGAAGTGCAGTTTA

TCTATCTTTATACATATATTTAAACTTTACTCTACGAATAATATAATCTATAGTACTA

CAATAATATCAGTGTTTTAGAGAATCATATAAATGAACAGTTAGACATGGTCTAAAG

GACAATTGAGTATTTTGACAACAGGACTCTACAGTTTTATCTTTTTAGTGTGCATGTG

TTCTCCTTTTTTTTGCAAATAGCTTCACCTATATAATACTTCATCCATTTTATTAGTA

CATCCATTTAGGGTTTAGGGTTAATGGTTTTTATAGACTAATTTTTTAGTACATCTA

TTTTATTCTATTTTAGCCTCTAAATTAAGAAAACTAAAACTCTATTTTAGTTTTTTTAT

TTAATAGTTTAGATATAAAATAGAATAAAATAAAGTGACTAAAAATTAAACAAATA

CCCTTTAAGAAATTAAAAAAACTAAGGAAACATTTTTCTTGTTTCGAGTAGATAATG

CCAGCCTGTTAAACGCCGTCGACGAGTCTAACGGACACCAACCAGCGAACCAGCAG

CGTCGCGTCGGGCCAAGCGAAGCAGACGGCACGGCATCTCTGTCGCTGCCTCTGGA

CCCCTCTCGAGAGTTCCGCTCCACCGTTGGACTTGCTCCGCTGTCGGCATCCAGAAA

TTGCGTGGCGGAGCGGCAGACGTGAGCCGGCACGGCAGGCGGCCTCCTCCTCCTCT

CACGGCACCGGCAGCTACGGGGGATTCCTTTCCCACCGCTCCTTCGCTTTCCCTTCCT

CGCCCGCCGTAATAAATAGACACCCCCTCCACACCCTCTT
```

In another embodiment, a promoter may comprise an upstream-promoter polynucleotide sequence from *Z. mays* c.v. B104 Ubi-1 gene as follows:

```
                                                     (SEQ ID NO: 4)
GACCCGGTCGTGCCCCTCTCTAGAGATAATGAGCATTGCATGTCTAAGTTATA

AAAAATTACCACATATTTTTTTGTCACACTTGTTTGAAGTGCAGTTTATCTATCTTT

ATACATATATTTAAACTTTACTCTACGAATAATATAATCTATAGTACTACAATAATAT

CAGTGTTTTAGAGAATCATATAAATGAACAGTTAGACATGGTCTAAAGGACAATTG

AGTATTTTGACAACAGGACTCTACAGTTTTATCTTTTTAGTGTGCATGTGTTCTCCTT

TTTTTTGCAAATAGCTTCACCTATATAATACTTCATCCATTTTATTAGTACATCCATT

TAGGGTTTAGGGTTAATGGTTTTTATAGACTAATTTTTTAGTACATCTATTTTATTCT

ATTTTAGCCTCTAAATTAAGAAAACTAAAACTCTATTTTAGTTTTTTTATTTAATAAT

TTAGATATAAAATAGAATAAAATAAAGTGACTAAAAATTAAACAAATACCCTTTAA

GAAATTAAAAAAACTAAGGAAACATTTTTCTTGTTTCGAGTAGATAATGCCAGCCTG

TTAAACGCCGTCGACGAGTCTAACGGACACCAACCAGCGAACCAGCAGCGTCGCGT

CGGGCCAAGCGAAGCAGACGGCACGGCATCTCTGTCGCTGCCTCTGGACCCCTCTCG

AGAGTTCCGCTCCACCGTTGGACTTGCTCCGCTGTCGGCATCCAGAAATTGCGTGGC

GGAGCGGCAGACGTGAGCCGGCACGGCAGGCGGCCTCCTCCTCCTCTCACGGCACC

GGCAGCTACGGGGGATTCCTTTCCCACCGCTCCTTCGCTTTCCCTTCCTCGCCCGCCG

TAATAAATAGACACCCCCTCCACACCCTCTT
```

Additional Gene Regulatory Elements

Transgene expression may also be regulated by a 5'-UTR and/or intron region located 3' downstream of the upstream-promoter sequence. A promoter comprising an upstream-promoter region operably linked to a 5'-UTR and/or intron can regulate transgene expression. While an upstream-promoter is necessary to drive transcription, the presence of a 5'-UTR and/or intron can increase expression levels resulting in the production of more mRNA transcripts for translation and protein synthesis. Addition of a 5'-UTR and/or intron to an upstream-promoter polynucleotide sequence can aid stable expression of a transgene.

In addition, a constitutive promoter comprising a upstream-promoter polynucleotide sequence may be followed by a 5-UTR or leader region to aid in the expression of transgenes in plants. In an embodiment, a promoter may comprise a 5'-UTR or leader polynucleotide sequence from Z. mays c.v. B73 Ubi-1 gene as follows:

```
                                              (SEQ ID NO: 5)
TCCCCAACCTCGTGTTGTTCGGAGCGCACACACACACAACCAGATCT

CCCCCAAATCCACCCGTCGGCACCTCCGCTTCAAG
```

In another embodiment, a promoter may comprise a 5'-UTR or leader polynucleotide sequence from Z. mays c.v. B104 Ubi-1 gene as follows:

```
                                              (SEQ ID NO: 6)
TCCCCAACCTCGTGTTGTTCGGAGCGCACACACACACAACCAGATCT

CCCCCAAATCCACCCGTCGGCACCTCCGCTTCAAG
```

Further, a constitutive promoter comprising an upstream-promoter polynucleotide sequence followed by a 5-UTR or leader region may also be followed by an intron to aid in expression of transgenes in plants. In an embodiment, a promoter may comprise an intronic polynucleotide sequence from Z. mays c.v. B73 Ubi-1 gene as follows:

```
                                              (SEQ ID NO: 7)
GTACGCCGCTCGTCCTCCCCCCCCCCCCCCCTCTCTACCTTCTCTAGA

TCGGCGTTCCGGTCCATGCATGGTTAGGGCCCGGTAGTTCTACTTCTGTTCATGTTTG

TGTTAGATCCGTGTTTGTGTTAGATCCGTGCTGCTAGCGTTCGTACACGGATGCGAC

CTGTACGTCAGACACGTTCTGATTGCTAACTTGCCAGTGTTTCTCTTTGGGGAATCCT

GGGATGGCTCTAGCCGTTCCGCAGACGGGATCGATTTCATGATTTTTTTGTTTCGTT

GCATAGGGTTTGGTTTGCCCTTTTCCTTTATTTCAATATATGCCGTGCACTTGTTTGTC

GGGTCATCTTTTCATGCTTTTTTTGTCTTGGTTGTGATGATGTGGTCTGGTTGGGCG

GTCGTTCTAGATCGGAGTAGAATTCTGTTTCAAACTACCTGGTGGATTTATTAATTTT

GGATCTGTATGTGTGTGCCATACATATTCATAGTTACGAATTGAAGATGATGGATGG

AAATATCGATCTAGGATAGGTATACATGTTGATGCGGGTTTTACTGATGCATATACA

GAGATGCTTTTTGTTCGCTTGGTTGTGATGATGTGGTGTGGTTGGGCGGTCGTTCATT

CGTTCTAGATCGGAGTAGAATACTGTTTCAAACTACCTGGTGTATTTATTAATTTTGG

AACTGTATGTGTGTGTCATACATCTTCATAGTTACGAGTTTAAGATGGATGGAAATA

TCGATCTAGGATAGGTATACATGTTGATGTGGGTTTTACTGATGCATATACATGATG

GCATATGCAGCATCTATTCATATGCTCTAACCTTGAGTACCTATCTATTATAATAAAC

AAGTATGTTTTATAATTATTTCGATCTTGATATACTTGGATGATGGCATATGCAGCAG

CTATATGTGGATTTTTTAGCCCTGCCTTCATACGCTATTTATTTGCTTGGTACTGTTT

CTTTTGTCGATGCTCACCCTGTTGTTTGGTGTTACTTCTGCA
```

In another embodiment, a promoter may comprise an intronic polynucleotide sequence from Z. mays c.v. B104 Ubi-1 gene as follows:

```
                                              (SEQ ID NO: 8)
GTACGCCGCTCGTCCTCCCCCCCCCCCTCTCTACCTTCTCTAGATCGG

CGTTCCGGTCCATGGTTAGGGCCCGGTAGTTCTACTTCTGTTCATGTTTGTGTTAGAT

CCGTGTTTGTGTTAGATCCGTGCTGCTAGCGTTCGTACACGGATGCGACCTGTACGT

CAGACACGTTCTGATTGCTAACTTGCCAGTGTTTCTCTTTGGGGAATCCTGGGATGG

CTCTAGCCGTTCCGCAGACGGGATCGATTTCATGATTTTTTTGTTTCGTTGCATAGG

GTTTGGTTTGCCCTTTTCCTTTATTTCAATATATGCCGTGCACTTGTTTGTCGGGTCAT
```

```
CTTTTCATGCTTTTTTTTGTCTTGGTTGTGATGATGTGGTCTGGTTGGGCGGTCGTTCT

AGATCGGAGTAGAATTCTGTTTCAAACTACCTGGTGGATTTATTAATTTTGGATCTGT

ATGTGTGTGCCATACATATTCATAGTTACGAATTGAAGATGATGGATGGAAATATCG

ATCTAGGATAGGTATACATGTTGATGCGGGTTTTACTGATGCATATACAGAGATGCT

TTTTGTTCGCTTGGTTGTGATGATGTGGTGTGGTTGGGCGGTCGTTCATTCGTTCTAG

ATCGGAGTAGAATACTGTTTCAAACTACCTGGTGTATTTATTAATTTTGGAACTGTAT

GTGTGTGTCATACATCTTCATAGTTACGAGTTTAAGATGGATGGAAATATCGATCTA

GGATAGGTATACATGTTGATGTGGGTTTTACTGATGCATATACATGATGGCATATGC

AGCATCTATTCATATGCTCTAACCTTGAGTACCTATCTATTATAATAAACAAGTATGT

TTTATAATTATTTTGATCTTGATATACTTGGATGATGGCATATGCAGCAGCTATATGT

GGATTTTTTAGCCCTGCCTTCATACGCTATTTATTTGCTTGGTACTGTTTCTTTTGTC

GATGCTCACCCTGTTGTTTGGTGTTACTTCTGCAG
```

Transgene and Reporter Gene Expression Cassettes

Transgene expression may also be regulated by a gene expression cassette. In an embodiment, a gene expression cassette comprises a promoter. In an embodiment, a gene expression cassette comprises an Ubi-1 promoter. In an embodiment, a gene expression cassette comprises an Ubi-1 promoter from a plant. In an embodiment, a gene expression cassette comprises an Ubi-1 promoter from Z. mays c.v. B104.

In an embodiment, a gene expression cassette comprises a Z. mays c.v. B104 Ubi-1 promoter, wherein the promoter is at least 80%, 85%, 90%, 91%, 92%, 93%, 94%, 95%, 96%, 97%, 98%, 99%, 99.5%, 99.8%, or 100% identical to SEQ ID NO: 2. In an embodiment, a gene expression cassette comprises a constitutive promoter, such as the Z. mays c.v. B104 Ubi-1 promoter, that is operably linked to a reporter gene or a transgene. In an embodiment, a gene expression cassette comprises a constitutive promoter that is operably linked to a transgene, wherein the transgene may be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof. In an embodiment, a gene expression cassette comprising the constitutive promoter may drive expression of one or more transgenes or reporter genes. In an embodiment, a gene expression cassette comprising the constitutive promoter may drive expression of two or more transgenes or reporter genes.

In an embodiment, a gene expression cassette comprises a Z. mays c.v. B104 Ubi-1 promoter, wherein the upstream-promoter sequence is at least 80%, 85%, 90%, 91%, 92%, 93%, 94%, 95%, 96%, 97%, 98%, 99%, 99.5%, 99.8%, or 100% identical to SEQ ID NO: 4. In an embodiment, a gene expression cassette comprises a constitutive promoter, such as the Z. mays c.v. B104 Ubi-1 upstream-promoter, that is operably linked to a reporter gene or a transgene. In an embodiment, a gene expression cassette comprises a constitutive upstream-promoter that is operably linked to a transgene, wherein the transgene may be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof. In an embodiment, a gene expression cassette comprising the constitutive upstream-promoter may drive expression of one or more transgenes or reporter genes. In an embodiment, a gene expression cassette comprising the constitutive upstream-promoter may drive expression of two or more transgenes or reporter genes. In a further embodiment, the upstream-promoter may comprise an intron. In an embodiment the upstream-promoter may comprise an intron sequence that is operably linked to a reporter gene or transgene. In another embodiment the upstream-promoter may comprise a 5'-UTR or leader sequence. In an embodiment the upstream-promoter may comprise a 5'-UTR or leader sequence that is operably linked to a reporter gene or transgene. In yet another embodiment the upstream-promoter may comprise a 5'-UTR or leader sequence and an intron sequence. In an embodiment the upstream-promoter may comprise a 5'-UTR or leader sequence and an intron sequence that are operably linked to a reporter gene or transgene.

In an embodiment, a gene expression cassette comprises a Z. mays c.v. B104 Ubi-1 promoter, wherein the 5'-UTR or leader sequence is at least 80%, 85%, 90%, 91%, 92%, 93%, 94%, 95%, 96%, 97%, 98%, 99%, 99.5%, 99.8%, or 100% identical to SEQ ID NO: 6. In an embodiment, a gene expression cassette comprises a 5'-UTR or leader from a maize gene encoding an Ubiquitin-1 protein that is operably linked to a promoter, wherein the promoter is a Z. mays c.v. B104 Ubi-1 promoter, or a promoter that originates from a plant (e.g., Zea mays Ubiquitin-1 promoter), a virus (e.g., Cassava vein mosaic virus promoter), or a bacteria (e.g., Agrobacterium tumefaciens delta mas). In an illustrative embodiment, a gene expression cassette comprises a Z. mays c.v. B104 5'-UTR or leader sequence from a maize gene encoding an Ubiquitin protein that is operably linked to a transgene, wherein the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof.

In an embodiment, a gene expression cassette comprises a Z. mays c.v. B104 Ubi-1 promoter, wherein the intronic sequence is at least 80%, 85%, 90%, 91%, 92%, 93%, 94%, 95%, 96%, 97%, 98%, 99%, 99.5%, 99.8%, or 100% identical to SEQ ID NO: 8. In an embodiment, a gene expression cassette comprises an intron from a maize gene encoding an Ubiquitin-1 protein that is operably linked to a promoter, wherein the promoter is a Z. mays c.v. B104 Ubi-1 promoter, or a promoter that originates from a plant (e.g., Zea mays Ubiquitin-1 promoter), a virus (e.g., Cassava vein mosaic virus promoter) or a bacteria (e.g., Agrobacterium tumefaciens delta mas). In an illustrative embodiment, a gene expression cassette comprises an intron from a maize gene encoding an Ubiquitin protein that is operably linked to a transgene, wherein the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof.

In an embodiment, a vector may comprise a gene expression cassette as described herein. In an embodiment, a vector may be a plasmid, a cosmid, a bacterial artificial chromosome (BAC), a bacteriophage, a virus, or an excised polynucleotide fragment for us in direct transformation or gene targeting, such as a donor DNA.

In an embodiment, a cell or plant comprises a gene expression cassette as described herein. In an embodiment, a cell or plant comprises a vector comprising a gene expression cassette as disclosed in this application. In an embodiment, a vector may be a plasmid, a cosmid, a bacterial artificial chromosome (BAC), a bacteriophage, or a virus. Thereby, a cell or plant comprising a gene expression cassette is a transgenic cell or a transgenic plant, respectively.

In an embodiment, a transgenic plant may be a monocotyledonous or a dicotyledonous plant. An embodiment of a transgenic monocotyledonous plant may be, but is not limited to maize, wheat, rice, sorghum, oats, rye, bananas, sugar cane, and millet. An embodiment of a transgenic dicotyledonous plant may be, but is not limited to soybean, cotton, sunflower, or canola. An embodiment also includes a transgenic seed from a transgenic plant, as described herein.

Selectable Markers

Various selectable markers, also described as reporter genes, may be incorporated into a chosen expression vector to allow for identification and selection of transformed plants ("transformants"). Many methods are available to confirm expression of selectable markers in transformed plants, including, for example, DNA sequencing and Polymerase Chain Reaction (PCR), Southern blotting, RNA blotting, immunological methods for detection of a protein expressed from the vector, such as, precipitated protein that mediates phosphinothricin resistance, or visual observation of other proteins such as reporter genes encoding β-Glucuronidase (GUS), Luciferase, Green Fluorescent Protein (GFP), Yellow Fluorescent Protein (YFP), DsRed, β-galactosidase, Chloramphenicol Acetyltransferase (CAT), alkaline phosphatase, and the like (See Sambrook, et al., Molecular Cloning: A Laboratory Manual, Third Edition, Cold Spring Harbor Press, N.Y., 2001, the content is incorporated herein by reference in its entirety).

Selectable marker genes are utilized for selection of transformed cells or tissues. Selectable marker genes include genes encoding antibiotic resistance, such as those encoding neomycin phosphotransferase II (NEO) and hygromycin phosphotransferase (HPT) as well as genes conferring resistance to herbicidal compounds. Herbicide resistance genes generally code for a modified target protein insensitive to the herbicide or for an enzyme that degrades or detoxifies the herbicide in the plant before it can act. For example, resistance to glyphosate has been obtained by using genes coding for mutant target enzymes, 5-enolpyruvylshikimate-3-phosphate synthase (EPSPS). Genes and mutants for EPSPS are well known, and further described below. Resistance to glufosinate ammonium, bromoxynil, and 2,4-dichlorophenoxyacetate (2,4-D) have been obtained by using bacterial genes encoding pat or DSM-2, a nitrilase, an aad-1 or an aad-12 gene, which detoxifies the respective herbicides.

In an embodiment, herbicides may inhibit the growing point or meristem, including imidazolinone or sulfonylurea, and genes for resistance/tolerance of acetohydroxyacid synthase (AHAS) and acetolactate synthase (ALS). Glyphosate resistance genes include mutant 5-enolpyruvylshikimate-3-phosphate synthase (EPSPs) and dgt-28 genes via the introduction of recombinant nucleic acids and/or various forms of in vivo mutagenesis of native EPSPs genes, aroA genes, and glyphosate acetyl transferase (GAT) genes, respectively. Resistance genes for other phosphono compounds include BAR genes from Streptomyces species, including Streptomyces hygroscopicus and Streptomyces viridichromogenes, and pyridinoxy or phenoxy proprionic acids and cyclohexones (ACCase inhibitor-encoding genes). Exemplary genes conferring resistance to cyclohexanediones and/or aryloxyphenoxypropanoic acid (including Haloxyfop, Diclofop, Fenoxyprop, Fluazifop, Quizalofop) include genes of acetyl coenzyme A carboxylase (ACCase)—Accl-S1, Accl-S2 and Accl-S3. In an embodiment, herbicides can inhibit photosynthesis, including triazine (psbA and 1s+ genes) or benzonitrile (nitrilase gene).

In an embodiment, selectable marker genes include, but are not limited to genes encoding: neomycin phosphotransferase II; cyanamide hydratase; aspartate kinase; dihydrodipicolinate synthase; tryptophan decarboxylase; dihydrodipicolinate synthase and desensitized aspartate kinase; bar gene; tryptophan decarboxylase; neomycin phosphotransferase (NEO); hygromycin phosphotransferase (HPT or HYG); dihydrofolate reductase (DHFR); phosphinothricin acetyltransferase; 2,2-dichloropropionic acid dehalogenase; acetohydroxyacid synthase; 5-enolpyruvyl-shikimate-phosphate synthase (aroA); haloarylnitrilase; acetyl-coenzyme A carboxylase; dihydropteroate synthase (sul I); and 32 kD photosystem II polypeptide (psbA).

An embodiment also includes genes encoding resistance to: chloramphenicol; methotrexate; hygromycin; spectinomycin; bromoxynil; glyphosate; and phosphinothricin.

The above list of selectable marker genes is not meant to be limiting. Any reporter or selectable marker gene is encompassed by the present invention.

Selectable marker genes are synthesized for optimal expression in plant. For example, in an embodiment, a coding sequence of a gene has been modified by codon optimization to enhance expression in plants. A selectable marker gene may be optimized for expression in a particular plant species or alternatively may be modified for optimal expression in dicotyledonous or monocotyledonous plants. Plant preferred codons may be determined from the codons of highest frequency in the proteins expressed in the largest amount in the particular plant species of interest. In an embodiment, a selectable marker gene is designed to be expressed in plants at a higher level resulting in higher transformation efficiency. Methods for plant optimization of genes are well known. Guidance regarding the optimization and manufacture of synthetic polynucleotide sequences may be found in, for example, WO2013/016546, WO2011/146524, WO1997/013402, U.S. Pat. No. 6,166,302, and U.S. Pat. No. 5,380,831, herein incorporated by reference.

Transgenes

The disclosed methods and compositions may be used to express polynucleotide gene sequences within the plant genome. Accordingly, genes encoding herbicide tolerance, insect resistance, nutrients, antibiotics, or therapeutic molecules may be expressed by the novel promoter.

In one embodiment the constitutive promoter regulatory element of the subject disclosure is combined or operably linked with one or more genes encoding polynucleotide sequences that provide resistance or tolerance to glyphosate, 2,4-D glufosinate, or another herbicide, provides resistance to select insects or diseases and/or nutritional enhancements, improved agronomic characteristics, proteins, or other products useful in feed, food, industrial, pharmaceutical or other uses. The transgenes may be "stacked" with two or more nucleic acid sequences of interest within a plant genome. Stacking may be accomplished, for example, via conventional plant breeding using two or more events, transformation of a plant with a construct which contains the sequences of interest, re-transformation of a transgenic plant, or addition of new traits through targeted integration via homologous recombination.

Such polynucleotide sequences of interest include, but are not limited to, those examples provided below:

1. Genes or Coding Sequence (e.g. iRNA) that Confer Resistance to Pests or Disease (A) Plant Disease Resistance Genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. Examples of such genes include, the tomato Cf-9 gene for resistance to *Cladosporium fulvum* (Jones et al., 1994 Science 266:789), tomato Pto gene, which encodes a protein kinase, for resistance to *Pseudomonas syringae* pv. tomato (Martin et al., 1993 Science 262:1432), and *Arabidopsis* RSSP2 gene for resistance to *Pseudomonas syringae* (Mindrinos et al., 1994 Cell 78:1089).

(B) A *Bacillus thuringiensis* protein, a derivative thereof or a synthetic polypeptide modeled thereon, such as, a nucleotide sequence of a Bt 67 -endotoxin gene (Geiser et al., 1986 Gene 48:109), and a vegetative insecticidal (VIP) gene (see, e.g., Estruch et al. (1996) Proc. Natl. Acad. Sci. 93:5389-94). Moreover, DNA molecules encoding 67 -endotoxin genes can be purchased from American Type Culture Collection (Rockville, Md.), under ATCC accession numbers 40098, 67136, 31995 and 31998.

(C) A lectin, such as, nucleotide sequences of several *Clivia miniata* mannose-binding lectin genes (Van Damme et al., 1994 Plant Molec. Biol. 24:825).

(D) A vitamin binding protein, such as avidin and avidin homologs which are useful as larvicides against insect pests. See U.S. Pat. No. 5,659,026.

(E) An enzyme inhibitor, e.g., a protease inhibitor or an amylase inhibitor. Examples of such genes include a rice cysteine proteinase inhibitor (Abe et al., 1987 J. Biol. Chem. 262:16793), a tobacco proteinase inhibitor I (Huub et al., 1993 Plant Molec. Biol. 21:985), and an α-amylase inhibitor (Sumitani et al., 1993 Biosci. Biotech. Biochem. 57:1243).

(F) An insect-specific hormone or pheromone such as an ecdysteroid and juvenile hormone a variant thereof, a mimetic based thereon, or an antagonist or agonist thereof, such as baculovirus expression of cloned juvenile hormone esterase, an inactivator of juvenile hormone (Hammock et al., 1990 Nature 344:458).

(G) An insect-specific peptide or neuropeptide which, upon expression, disrupts the physiology of the affected pest (J. Biol. Chem. 269:9). Examples of such genes include an insect diuretic hormone receptor (Regan, 1994), an allostatin identified in *Diploptera punctata* (Pratt, 1989), and insect-specific, paralytic neurotoxins (U.S. Pat. No. 5,266,361).

(H) An insect-specific venom produced in nature by a snake, a wasp, etc., such as a scorpion insectotoxic peptide (Pang, 1992 Gene 116:165).

(I) An enzyme responsible for a hyperaccumulation of monoterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. Examples of such genes include, a callas gene (PCT published application WO93/02197), chitinase-encoding sequences (which can be obtained, for example, from the ATCC under accession numbers 3999637 and 67152), tobacco hookworm chitinase (Kramer et al., 1993 Insect Molec. Biol. 23:691), and parsley ubi4-2 polyUbiquitin gene (Kawalleck et al., 1993 Plant Molec. Biol. 21:673).

(K) A molecule that stimulates signal transduction. Examples of such molecules include nucleotide sequences for mung bean calmodulin cDNA clones (Botella et al., 1994 Plant Molec. Biol. 24:757) and a nucleotide sequence of a maize calmodulin cDNA clone (Griess et al., 1994 Plant Physiol. 104:1467).

(L) A hydrophobic moment peptide. See U.S. Pat. Nos. 5,659,026 and 5,607,914; the latter teaches synthetic antimicrobial peptides that confer disease resistance.

(M) A membrane permease, a channel former or a channel blocker, such as a cecropin-β lytic peptide analog (Jaynes et al., 1993 Plant Sci. 89:43) which renders transgenic tobacco plants resistant to *Pseudomonas solanacearum*.

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. See, for example, Beachy et al. (1990) Ann. Rev. Phytopathol. 28:451.

(O) An insect-specific antibody or an immunotoxin derived therefrom. Thus, an antibody targeted to a critical metabolic function in the insect gut would inactivate an affected enzyme, killing the insect. For example, Taylor et al. (1994) Abstract #497, Seventh Int'l. Symposium on Molecular Plant-Microbe Interactions shows enzymatic inactivation in transgenic tobacco via production of single-chain antibody fragments.

(P) A virus-specific antibody. See, for example, Tavladoraki et al. (1993) Nature 266:469, which shows that transgenic plants expressing recombinant antibody genes are protected from virus attack.

(Q) A developmental-arrestive protein produced in nature by a pathogen or a parasite. Thus, fungal endo α-1,4-D polygalacturonases facilitate fungal colonization and plant nutrient release by solubilizing plant cell wall homo-α-1,4-D-galacturonase (Lamb et al., 1992) Bio/Technology 10:1436. The cloning and characterization of a gene which encodes a bean endopolygalacturonase-inhibiting protein is described by Toubart et al. (1992 Plant J. 2:367).

(R) A developmental-arrestive protein produced in nature by a plant, such as the barley ribosome-inactivating gene that provides an increased resistance to fungal disease (Longemann et al., 1992). Bio/Technology 10:3305.

(S) RNA interference, in which an RNA molecule is used to inhibit expression of a target gene. An RNA molecule in one example is partially or fully double stranded, which triggers a silencing response, resulting in cleavage of dsRNA into small interfering RNAs, which are then incorporated into a targeting complex that destroys homologous mRNAs. See, e.g., Fire et al., U.S. Pat. No. 6,506,559; Graham et al, U.S. Pat. No. 6,573,099.

2. Genes that Confer Resistance to a Herbicide (A) Genes encoding resistance or tolerance to a herbicide that inhibits the growing point or meristem, such as an imidazalinone, sulfonanilide or sulfonylurea herbicide. Exemplary genes in this category code for mutant acetolactate synthase (ALS) (Lee et al., 1988 EMBO J. 7:1241) also known as acetohydroxyacid synthase (AHAS) enzyme (Miki et al., 1990 Theor. Appl. Genet. 80:449).

(B) One or more additional genes encoding resistance or tolerance to glyphosate imparted by mutant EPSP synthase and aroA genes, or through metabolic inactivation by genes such as DGT-28, 2mEPSPS, GAT (glyphosate acetyltransferase) or GOX (glyphosate oxidase) and other phosphono compounds such as glufosinate (pat, bar, and dsm-2 genes), and aryloxyphenoxypropionic acids and cyclohexanediones (ACCase inhibitor encoding genes). See, for example, U.S. Pat. No. 4,940,835, which discloses the nucleotide sequence of a form of EPSP which can confer glyphosate resistance. A DNA molecule encoding a mutant aroA gene can be obtained under ATCC Accession Number 39256, and the nucleotide sequence of the mutant gene is disclosed in U.S. Pat. No. 4,769,061. European Patent Application No. 0 333 033 and U.S. Pat. No. 4,975,374 disclose nucleotide sequences of glutamine synthetase genes which confer resistance to herbicides such as L-phosphinothricin. The nucleotide sequence of a phosphinothricinacetyl-transferase gene is provided in European Patent Application No. 0 242 246. De Greef et al. (1989) Bio/Technology 7:61 describes the production of transgenic plants that express chimeric bar genes coding for phosphinothricin acetyl transferase activity. Exemplary of genes conferring resistance to aryloxyphenoxypropionic acids and cyclohexanediones, such as sethoxydim and haloxyfop, are the Accl-S1, Accl-S2 and Accl-S3 genes described by Marshall et al. (1992) Theor. Appl. Genet. 83:435.

(C) Genes encoding resistance or tolerance to a herbicide that inhibits photosynthesis, such as a triazine (psbA and gs+ genes) and a benzonitrile (nitrilase gene). Przibilla et al. (1991) Plant Cell 3:169 describe the use of plasmids encoding mutant psbA genes to transform *Chlamydomonas*. Nucleotide sequences for nitrilase genes are disclosed in U.S. Pat. No. 4,810,648, and DNA molecules containing these genes are available under ATCC accession numbers 53435, 67441 and 67442. Cloning and expression of DNA coding for a glutathione S-transferase is described by Hayes et al. (1992) Biochem. J. 285:173.

(D) Genes encoding resistance or tolerance to a herbicide that bind to hydroxyphenylpyruvate dioxygenases (HPPD), enzymes which catalyze the reaction in which para-hydroxyphenylpyruvate (HPP) is transformed into homogentisate. This includes herbicides such as isoxazoles (EP418175, EP470856, EP487352, EP527036, EP560482, EP682659, U.S. Pat. No. 5,424,276), in particular isoxaflutole, which is a selective herbicide for maize, diketonitriles (EP496630, EP496631), in particular 2-cyano-3-cyclopropyl-1-(2-SO2CH3-4-CF3 phenyl)propane-1,3-dione and 2-cyano-3-cyclopropyl-1-(2-SO2CH3-4-2,3Cl2phenyl)propane-1,3-dione, triketones (EP625505, EP625508, U.S. Pat. No. 5,506,195), in particular sulcotrione, and pyrazolinates. A gene that produces an overabundance of HPPD in plants can provide tolerance or resistance to such herbicides, including, for example, genes described in U.S. Pat. Nos. 6,268,549 and 6,245,968 and U.S. Patent Application Publication No. 2003/0066102.

(E) Genes encoding resistance or tolerance to phenoxy auxin herbicides, such as 2,4-dichlorophenoxyacetic acid (2,4-D) and which may also confer resistance or tolerance to aryloxyphenoxypropionate (AOPP) herbicides. Examples of such genes include the □-ketoglutarate-dependent dioxygenase enzyme (aad-1) gene, described in U.S. Pat. No. 7,838,733.

(F) Genes encoding resistance or tolerance to phenoxy auxin herbicides, such as 2,4-dichlorophenoxyacetic acid (2,4-D) and which may also confer resistance or tolerance to pyridyloxy auxin herbicides, such as fluroxypyr or triclopyr. Examples of such genes include the α-ketoglutarate-dependent dioxygenase enzyme gene (aad-12), described in WO2007/053482 A2.

(G) Genes encoding resistance or tolerance to dicamba (see, e.g., U.S. Patent Publication No. 20030135879).

(H) Genes providing resistance or tolerance to herbicides that inhibit protoporphyrinogen oxidase (PPO) (see U.S. Pat. No. 5,767,373).

(I) Genes providing resistance or tolerance to triazine herbicides (such as atrazine) and urea derivatives (such as diuron) herbicides which bind to core proteins of photosystem II reaction centers (PS II) (See Brussian et al., (1989) EMBO J. 1989, 8(4): 1237-1245.

3. Genes that Confer or Contribute to a Value-Added Trait (A) Modified fatty acid metabolism, for example, by transforming maize or *Brassica* with an antisense gene or stearoyl-ACP desaturase to increase stearic acid content of the plant (Knultzon et al., 1992) Proc. Nat. Acad. Sci. USA 89:2624.

(B) Decreased phytase content (1) Introduction of a phytase-encoding gene, such as the *Aspergillus niger* phytase gene (Van Hartingsveldt et al., 1993 Gene 127:87), enhances breakdown of phytate, adding more free phosphate to the transformed plant.

(2) A gene could be introduced that reduces phytate content. In maize, this, for example, could be accomplished by cloning and then reintroducing DNA associated with the single allele which is responsible for maize mutants characterized by low levels of phytic acid (Raboy et al., 1990 Maydica 35:383).

(C) Modified carbohydrate composition effected, for example, by transforming plants with a gene coding for an enzyme that alters the branching pattern of starch. Examples of such enzymes include, *Streptococcus* mucus fructosyltransferase gene (Shiroza et al., 1988) J. Bacteriol. 170:810, *Bacillus subtilis* levansucrase gene (Steinmetz et al., 1985 Mol. Gen. Genel. 200:220), *Bacillus licheniformis* α-amylase (Pen et al., 1992 Bio/Technology 10:292), tomato invertase genes (Elliot et al., 1993), barley amylase gene (Sogaard et al., 1993 J. Biol. Chem. 268:22480), and maize endosperm starch branching enzyme II (Fisher et al., 1993 Plant Physiol. 102:10450).

Transformation

Suitable methods for transformation of plants include any method where DNA may be introduced into a cell, for example and without limitation: electroporation (see, e.g., U.S. Pat. No. 5,384,253); micro-projectile bombardment (see, e.g., U.S. Pat. Nos. 5,015,580; 5,550,318; 5,538,880; 6,160,208; 6,399,861; and 6,403,865); *Agrobacterium*-mediated transformation (see, e.g., U.S. Pat. Nos. 5,635,055; 5,824,877; 5,591,616; 5,981,840; and 6,384,301); and protoplast transformation (see, e.g., U.S. Pat. No. 5,508,184). These methods may be used to stably transform or transiently transform a plant.

A DNA construct may be introduced directly into the genomic DNA of the plant cell using techniques such as agitation with silicon carbide fibers (See, e.g., U.S. Pat. Nos. 5,302,523 and 5,464,765). DNA constructs may be introduced directly into plant tissue using biolistic methods, such as DNA particle bombardment (see, e.g., Klein et al., (1987) Nature 327:70-73). Alternatively, DNA constructs may be introduced into the plant cell via nanoparticle transformation (see, e.g., U.S. Patent Publication No. 2009/0104700, incorporated herein by reference in its entirety).

In addition, gene transfer may be achieved using non-*Agrobacterium* bacteria or viruses, such as *Rhizobium* sp. NGR234, *Sinorhizoboium meliloti*, *Mesorhizobium loti*, potato virus X, cauliflower mosaic virus, cassava vein mosaic virus, and/or tobacco mosaic virus, see, e.g., Chung et al. (2006) *Trends Plant Sci.* 11(1):1-4.

Through the application of transformation techniques, cells of virtually any plant species may be stably transformed, and these cells may be developed into transgenic plants by well-known techniques. For example, techniques that may be particularly useful in the context of cotton transformation are described in U.S. Pat. Nos. 5,846,797; 5,159,135; 5,004,863; and 6,624,344; techniques for transforming *Brassica* plants in particular are described, for example, in U.S. Pat. No. 5,750,871; techniques for transforming soybean are described, for example, in U.S. Pat. No. 6,384,301; and techniques for transforming maize are described, for example, in U.S. Pat. Nos. 7,060,876 and 5,591,616, and International PCT Publication WO95/06722.

After effecting delivery of an exogenous nucleic acid to a recipient cell, a transformed cell is generally identified for further culturing and plant regeneration. In order to improve the ability to identify transformants, one may desire to employ a selectable marker gene with the transformation vector used to generate the transformant. In an illustrative embodiment, a transformed cell population may be assayed by exposing the cells to a selective agent or agents, or the cells may be screened for the desired marker gene trait.

Cells that survive exposure to a selective agent, or cells that have been scored positive in a screening assay, may be cultured in media that supports regeneration of plants. In an embodiment, any suitable plant tissue culture media may be modified by including further substances, such as growth regulators. Plant tissues may be maintained on a basic media with growth regulators until sufficient tissue is available to begin plant regeneration efforts. Alternatively, following repeated rounds of manual selection, until the morphology of the tissue is suitable for regeneration (e.g., at least 2 weeks), the tissue may then be transferred to media conducive to shoot formation. Cultures are transferred periodically until sufficient shoot formation has occurred. Once shoots are formed, they are transferred to media conducive to root formation. Once sufficient roots are formed, plants may be transferred to soil for further growth and maturity.

To confirm the presence of a desired nucleic acid comprising constructs provided in regenerating plants, a variety of assays may be performed. Such assays may include: molecular biological assays, such as Southern and Northern blotting and PCR; biochemical assays, such as detecting the presence of a protein product by immunological means, such as, ELISA, western blots, and/or LC-MS MS spectrophotometry) or by enzymatic function, such as, by plant part assays, such as leaf, callus, or pollen assays; and/or analysis of the phenotype of the whole regenerated plant.

Transgenic events may be screened, for example, by PCR amplification using oligonucleotide primers specific for nucleic acid molecules of interest. PCR genotyping is understood to include, but not be limited to, PCR amplification of genomic DNA derived from isolated and/or purified host plant tissue predicted to contain a nucleic acid molecule of interest integrated into the genome, followed by standard cloning, and sequence analysis of PCR amplification products. Methods of PCR genotyping have been well described (see, e.g., Rios et al. (2002) Plant J. 32:243-53) and may be applied to genomic DNA derived from any plant species or tissue type, including cell cultures.

Combinations of oligonucleotide primers that bind to both target sequence and introduced sequence may be used sequentially or multiplexed in PCR amplification reactions. Oligonucleotide primers designed to anneal to the target site, introduced nucleic acid sequences, and/or combinations of the two types of nucleic acid sequences may be produced. Thus, PCR genotyping strategies may include, for example and without limitation: amplification of specific sequences in the plant genome; amplification of multiple specific sequences in the plant genome; amplification of non-specific sequences in the plant genome; and combinations of any of the foregoing. One skilled in the art may devise additional combinations of primers and amplification reactions to interrogate the genome. For example, a set of forward and reverse oligonucleotide primers may be designed to anneal to nucleic acid sequence(s) specific for the target outside the boundaries of the introduced nucleic acid sequence.

Forward and reverse oligonucleotide primers may be designed to anneal specifically to an introduced nucleic acid molecule, for example, at a sequence corresponding to a coding region within a nucleotide sequence of interest comprised therein, or other parts of the nucleic acid molecule. Primers may be used in conjunction with primers described herein. Oligonucleotide primers may be synthesized according to a desired sequence and are commercially available (e.g., from Integrated DNA Technologies, Inc., Coralville, Iowa). Amplification may be followed by cloning and sequencing, or by direct sequence analysis of amplification products. In an embodiment, oligonucleotide primers specific for the gene target are employed in PCR amplifications.

Method of Expressing a Transgene

In an embodiment, a method of expressing at least one transgene in a plant comprises growing a plant comprising a *Z. mays* c.v. B104 Ubi-1 promoter (SEQ ID NO: 2) operably linked to at least one transgene. In an embodiment, a method of expressing at least one transgene in a plant tissue or plant cell comprises culturing a plant tissue or plant cell comprising a *Z. mays* c.v. B104 Ubi-1 promoter (SEQ ID NO: 2) operably linked to at least one transgene.

In an embodiment, a method of expressing at least one transgene in a plant comprises growing a plant comprising a gene expression cassette comprising a *Z. mays* c.v. B104 Ubi-1 promoter (SEQ ID NO: 2) operably linked to at least one transgene. In another embodiment, a method of expressing at least one transgene in a plant tissue or plant cell comprises culturing a plant tissue or plant cell comprising a gene expression cassette comprising a *Z. mays* c.v. B104 Ubi-1 promoter (SEQ ID NO: 2) operably linked to at least one transgene.

In an embodiment, a plant, plant tissue, or plant cell comprises a gene expression cassette comprising a *Z. mays* c.v. B104 Ubi-1 promoter (SEQ ID NO: 2) operably linked to a transgene. Wherein, the *Z. mays* c.v. B104 Ubi-1 promoter (SEQ ID NO: 2) is comprised of an upstream-promoter (SEQ ID NO: 4), 5'-UTR (SEQ ID NO: 6), and an intron (SEQ ID NO: 8). In an embodiment, a plant, plant tissue, or plant cell comprises a gene expression cassette comprising a *Z. mays* c.v. B104 Ubi-1 upstream-promoter (SEQ ID NO: 4), 5'-UTR (SEQ ID NO: 6), and an intron (SEQ ID NO: 8). In an embodiment, a plant, plant tissue, or plant cell comprises a gene expression cassette comprising a *Z. mays* c.v. B104 Ubi-1 upstream-promoter (SEQ ID NO: 4), 5'-UTR (SEQ ID NO: 6), and an intron (SEQ ID NO: 8) of a *Z. mays* c.v. B104 Ubi-1 gene. In an embodiment, a plant, plant tissue, or plant cell comprises a gene expression cassette comprising a *Z. mays* c.v. B104 Ubi-1 upstream-promoter (SEQ ID NO: 4), 5'-UTR (SEQ ID NO: 6), and an intron (SEQ ID NO: 8) of a *Z. mays* c.v. B104 Ubi-1 gene.

In an embodiment, a plant, plant tissue, or plant cell comprises a *Z. mays* c.v. B104 Ubi-1 promoter. In an embodiment, a *Z. mays* c.v. B104 Ubi-1 promoter may be SEQ ID NO: 2. In an embodiment, a plant, plant tissue, or plant cell comprises a gene expression cassette comprising a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO: 2. In an embodiment, a plant, plant tissue, or plant cell comprises a gene expression cassette comprising a *Z. mays* c.v. B104 Ubi-1 promoter that is operably linked to a transgene. In an illustrative embodiment, a plant, plant tissue, or plant cell comprises a gene expression cassette comprising a *Z. mays* c.v. B104 Ubi-1 promoter that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof. In an embodiment, a plant, plant tissue, or plant cell comprises a *Z. mays* c.v. B104 Ubi-1 upstream-promoter. In an embodiment, a *Z. mays* c.v. B104 Ubi-1 upstream-promoter may be SEQ ID NO: 4. In an embodiment, a plant, plant tissue, or plant cell comprises a gene expression cassette comprising an upstream-promoter, wherein the upstream-promoter is at least 80%, 85%, 90%, 91%, 92%, 93%, 94%, 95%, 96%, 97%, 98%, 99%, 99.5%, 99.8%, or 100% identical to SEQ ID NO: 4. In an embodiment, a plant, plant tissue, or plant cell comprises a gene expression cassette comprising a *Z. mays* c.v. B104 Ubi-1 upstream-promoter that is operably linked to a transgene. In an illustrative embodiment, a plant, plant tissue, or plant cell comprises a gene expression cassette comprising a *Z. mays* c.v. B104 Ubi-1 upstream-promoter that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In an embodiment, a plant, plant tissue, or plant cell comprises a *Z. mays* c.v. B104 Ubi-1 5'-UTR or leader sequence. In an embodiment, a *Z. mays* c.v. B104 Ubi-1 5'-UTR or leader sequence may be a polynucleotide of SEQ ID NO: 6. In an embodiment, a plant, plant tissue, or plant cell comprises a gene expression cassette comprising a 5'-UTR or leader sequence, wherein the 5'-UTR or leader sequence is at least 80%, 85%, 90%, 91%, 92%, 93%, 94%, 95%, 96%, 97%, 98%, 99%, 99.5%, 99.8%, or 100% identical to SEQ ID NO: 6. In an embodiment, a gene expression cassette comprises a *Z. mays* c.v. B104 Ubi-1 5'-UTR or leader that is operably linked to a promoter, wherein the promoter is an Ubiquitin promoter, or a promoter that originates from a plant (e.g., *Zea mays* Ubiquitin-1 promoter), a virus (e.g., Cassava vein mosaic virus promoter) or a bacteria (e.g., *Agrobacterium tumefaciens* delta mas). In an embodiment, a plant, plant tissue, or plant cell comprises a gene expression cassette comprising a *Z. mays* c.v. B104 Ubi-1 5'-UTR or leader that is operably linked to a transgene. In an illustrative embodiment, a plant, plant tissue, or plant cell comprising a gene expression cassette comprising a *Z. mays* c.v. B104 Ubi-1 5'-UTR or leader that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In an embodiment, a plant, plant tissue, or plant cell comprises an Ubi-1 intron. In an embodiment, a plant, plant tissue, or plant cell comprises a *Z. mays* c.v. B104 Ubi-1 intron. In an embodiment, a *Z. mays* c.v. B104 Ubi-1 intron may be a polynucleotide of SEQ ID NO: 8. In an embodiment, a plant, plant tissue, or plant cell comprises a gene expression cassette comprising an intron, wherein the intron is at least 80%, 85%, 90%, 91%, 92%, 93%, 94%, 95%, 96%, 97%, 98%, 99%, 99.5%, 99.8%, or 100% identical to SEQ ID NO: 8. In an embodiment, a gene expression cassette comprises a *Z. mays* c.v. B104 Ubi-1 intron that is operably linked to a promoter, wherein the promoter is an Ubiquitin promoter, or a promoter that originates from a plant (e.g., *Zea mays* Ubiquitin-1 promoter), a virus (e.g., Cassava vein mosaic virus promoter) or a bacteria (e.g., *Agrobacterium tumefaciens* delta mas). In an embodiment, a plant, plant tissue, or plant cell comprises a gene expression cassette comprising a *Z. mays* c.v. B104 Ubi-1 intron that is operably linked to a transgene. In an illustrative embodiment, a plant, plant tissue, or plant cell comprising a gene expression cassette comprising a *Z. mays* c.v. B104 Ubi-1 intron that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In an embodiment, a plant, plant tissue, or plant cell comprises a gene expression cassette comprising a *Z. mays* c.v. B104 Ubi-1 upstream-promoter, Ubi-1 intron, and an Ubi-1 5'-UTR that are operably linked to a transgene. The *Z. mays* c.v. B104 Ubi-1 promoter, Ubi-1 intron, and an Ubi-1 5'-UTR can be operably linked to different transgenes within a gene expression cassette when a gene expression cassette includes two or more transgenes. In an illustrative embodiment, a gene expression cassette comprises a *Z. mays* c.v. B104 Ubi-1 promoter that is operably linked to a transgene, wherein the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof. In an illustrative embodiment, a gene expression cassette comprises a *Z. mays* c.v. B104 Ubi-1 intron that is operably linked to a transgene, wherein the transgene can be an insecticidal resistance transgene, an herbicide tolerance transgene, a nitrogen use efficiency transgene, a water us efficiency transgene, a nutritional quality transgene, a DNA binding transgene, a selectable marker transgene, or combinations thereof. In an embodiment, a gene expression cassette comprises a Z. mays c.v. B104 Ubi-1 intron that is operably linked to a promoter, wherein the promoter is an Ubiquitin promoter, or a promoter that originates from a plant (e.g., Zea mays Ubiquitin-1 promoter), a virus (e.g., Cassava vein mosaic virus promoter) or a bacterium (e.g., Agrobacterium tumefaciens delta mas). In an illustrative embodiment, a gene expression cassette comprises a Z. mays c.v. B104 Ubi-1 5'-UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In an embodiment, a plant, plant tissue, or plant cell comprises a vector comprising a constitutive gene promoter regulatory element as disclosed herein. In an embodiment, a plant, plant tissue, or plant cell comprises a vector comprising a constitutive gene promoter regulatory element, as disclosed herein, operably linked to a transgene. In an embodiment, a plant, plant tissue, or plant cell comprises a vector comprising a gene expression cassette, as disclosed herein. In an embodiment, a vector may be a plasmid, a cosmid, a bacterial artificial chromosome (BAC), a bacteriophage, or a virus fragment.

In an embodiment, a plant, plant tissue, or plant cell, according to the methods disclosed herein, may be monocotyledonous. The monocotyledonous plant, plant tissue, or plant cell may be, but is not limited to corn, rice, wheat, sugarcane, barley, rye, sorghum, orchids, bamboo, banana, cattails, lilies, oat, onion, millet, and triticale. In another embodiment, a plant, plant tissue, or plant cell, according to the methods disclosed herein, may be dicotyledonous. The dicotyledonous plant, plant tissue, or plant cell may be, but is not limited to rapeseed, canola, Indian mustard, Ethiopian mustard, soybean, sunflower, and cotton.

With regard to the production of genetically modified plants, methods for the genetic engineering of plants are well known in the art. For instance, numerous methods for plant transformation have been developed, including biological and physical transformation protocols for dicotyledonous plants as well as monocotyledonous plants (e.g., Goto-Fumiyuki et al., *Nature Biotech* 17:282-286 (1999); Miki et al., Methods in Plant Molecular Biology and Biotechnology, Glick, B. R. and Thompson, J. E. Eds., CRC Press, Inc., Boca Raton, pp. 67-88 (1993)). In addition, vectors and in vitro culture methods for plant cell or tissue transformation and regeneration of plants are available, for example, in Gruber et al., Methods in Plant Molecular Biology and Biotechnology, Glick, B. R. and Thompson, J. E. Eds., CRC Press, Inc., Boca Raton, pp. 89-119 (1993).

One of ordinary skill in the art will recognize that after the exogenous sequence is stably incorporated in transgenic plants and confirmed to be operable, it may be introduced into other plants by sexual crossing. Any of a number of standard breeding techniques may be used, depending upon the species to be crossed.

A transformed plant cell, root, leaf, callus, pollen, tissue, or plant may be identified and isolated by selecting or screening the engineered plant material for traits encoded by the marker genes present on the transforming DNA. For example, selection may be performed by growing the engineered plant material on media containing an inhibitory amount of an antibiotic or herbicide to which the transforming gene construct confers resistance. Further, transformed cells may also be identified by screening for the activities of any visible marker genes (e.g., the YFP, GFP, β-glucuronidase, Luciferase, B or C1 genes) that may be present on the recombinant nucleic acid constructs. Such selection and screening methodologies are well known to those of ordinary skill in the art.

Physical and biochemical methods also may be used to identify plant or plant cell transformants containing inserted gene constructs. These methods include, but are not limited to: 1) Southern analysis or PCR amplification for detecting and determining the structure of the recombinant DNA insert; 2) Northern blot, S1 RNase protection, primer-extension, or reverse transcriptase-PCR amplification for detecting and examining RNA transcripts of the gene constructs; 3) enzymatic assays for detecting enzyme or ribozyme activity, where such gene products are encoded by the gene construct; 4) next generation sequencing (NGS) analysis; or 5) protein gel electrophoresis, western blot techniques, immunoprecipitation, or enzyme-linked immunosorbent assay (ELISA), where the gene construct products are proteins. Additional techniques, such as in situ hybridization, enzyme staining, and immunostaining, may also be used to detect the presence or expression of the recombinant construct in specific plant organs and tissues. The methods for doing all of these assays are well known to those skilled in the art.

Effects of gene manipulation using the methods disclosed herein may be observed by, for example, Northern blots of the RNA (e.g., mRNA) isolated from the tissues of interest. Typically, if the mRNA is present or the amount of mRNA has increased, it may be assumed that the corresponding transgene is being expressed. Other methods of measuring gene and/or encoded polypeptide activity may be used. Different types of enzymatic assays may be used, depending on the substrate used and the method of detecting the increase or decrease of a reaction product or by-product. In addition, the levels of polypeptide expressed may be measured immunochemically, by employing ELISA, RIA, EIA, and other antibody based assays well known to those of skill in the art, such as, by electrophoretic detection assays (either with staining or western blotting). As one non-limiting example, the detection of the AAD-1 (aryloxyalkanoate dioxygenase; see WO 2005/107437) and PAT (phosphinothricin-N-acetyl-transferase) proteins using an ELISA assay is described in U.S. Patent Publication No. 20090093366 which is incorporated herein by reference in its entirety. The transgene may also be selectively expressed in some cell types or tissues of the plant or at some developmental stages. The transgene may also be substantially expressed in all plant tissues and along its entire life cycle. However, any combinatorial expression mode is also applicable.

The present disclosure also encompasses seeds of the transgenic plants described above, wherein the seed comprises the reporter gene, transgene, or gene expression cassette. The present disclosure further encompasses the progeny, clones, cell lines, or cells of the transgenic plants described above, wherein said progeny, clone, cell line, or cell comprises the reporter gene, transgene, or gene construct.

While the invention has been described with reference to specific methods and embodiments, it should be appreciated that various modifications and changes may be made without departing from the invention described herein.

EXAMPLES

Example 1

Novel Promoter Identification and Isolation

A novel promoter sequence from the Ubi-1 gene of *Zea mays* c.v. B104 was amplified using Polymerase Chain Reaction (PCR). Oligonucleotides (Table 1) designed to amplify the novel promoter, *Z. mays* c.v. B104, were derived from conserved regions of the *Z. mays* c.v. B73 Ubi-1 promoter sequence, which served as the control. A PCR product was obtained from *Z. mays* c.v. B104 and was characterized.

Figure 2:
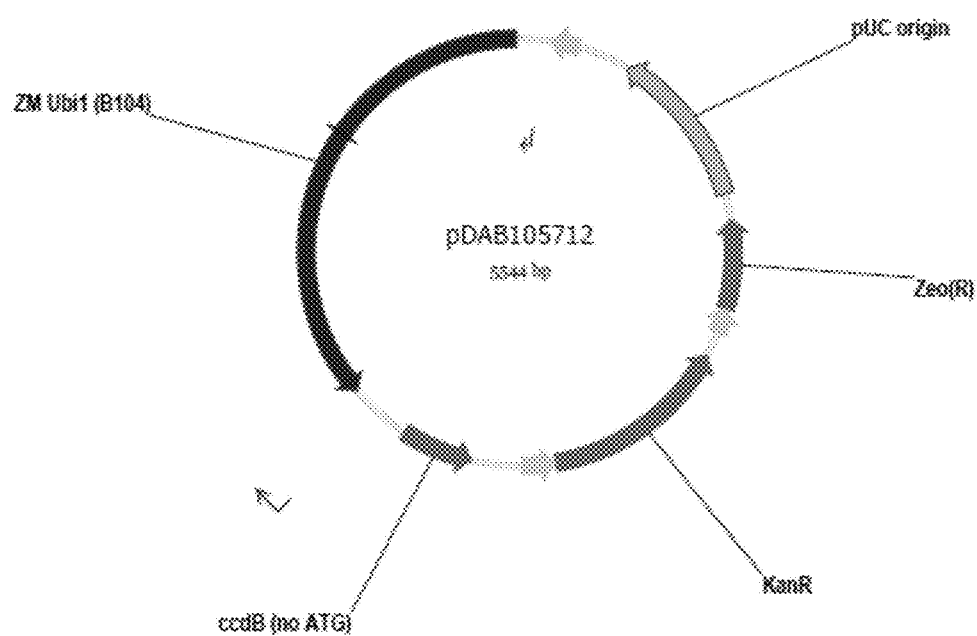
FIG. 2 shows the plasmid map for vector pDAB105712 comprising the PCR amplified promoter sequence of *Z. mays* c.v. B104 Ubi-1 gene.

The PCR product comprising the novel promoter was cloned into Topo™ vectors using Invitrogen Zero Blunt® TOPO® PCR Cloning Kit according to manufacturer's instructions. A vector map showing the cloned plasmid comprising the novel promoter PCR product is provided. Plasmid pDAB105712 corresponds to *Z. mays* c.v. B104 (FIG. 2).

| Primers used for PCR Amplification of Novel Ubi-1 Promoters | |
|---|---|
| | Seq. ID No: |
| Forward Primer: GCTACCGCGG<u>ACCCGGTCGTGCCCCT CTCTAGAGATAATG</u> | 9 |
| Reverse Primer: AGTCAGGTACC<u>CTGCAGAAGTAACAC CAAACAACAG</u> | 10 |

The promoter-specific sequence of the PCR primers is underlined.
The primer sequence located 5' upstream of the promoter-specific sequence is linker sequence used for cloning.

After cloning, the promoter insert containing the PCR product was sequenced using methods known to those skilled in the art. The promoter polynucleotide sequences of *Z. mays* c.v. B104 (FIG. 4) was computationally aligned and subsequently analyzed for sequence homology to the *Z. mays* c.v. B73 Ubi-1 control sequence (FIG. 3). Bioinformatic methods and/or software programs known by those skilled in the art, such as ClustalW or Sequencher, were used to perform the sequence homology analysis.

Example 2

Novel Promoter Characterization

Sequence homology analysis (FIGS. 3-7), including sequence alignment and comparison to the *Z. mays* c.v. B73 Ubi-1 control sequence (SEQ ID NO: 1; FIG. 3) revealed a novel Ubi-1 promoter for further characterization. It was also observed that the new Ubi-1 promoter sequence, obtained from *Z. mays* c.v. B104 (SEQ ID NO: 2; FIG. 4), comprised polynucleotide sequences of three distinct regions; 1) an upstream-promoter region (SEQ ID NO: 4), 2) a 5'-UTR (SEQ ID NO: 6), and 3) an intron (SEQ ID NO: 8). The promoter regions and specific promoter elements from *Z. mays* c.v. B104 were analyzed for sequence homology to the *Z. mays* c.v. B73 Ubi-1 control sequence (FIGS. 5-7). More specifically, sequence alignment was performed to independently compare the upstream-promoter, 5'-UTR, and intronic regions, as well as the TATA Box and Heat Shock Element (HSE) regulatory elements of the *Z. mays* c.v. B104 promoter to the corresponding regions of the *Z. mays* c.v. B73 Ubi-1 control sequence (FIGS. 5-7, Table 2).

TABLE 2

Sequence Homology (%) between *Z. mays* c.v. B73 Ubi-1 Promoter and Novel Ubi-1 Promoter

| Promoter | Total | Upstream-Promoter | 5'-UTR/ Leader | Intron | TATA Box | Heat Shock Element |
|---|---|---|---|---|---|---|
| *Z. mays* c.v. B104 | 85.7 | 93.4 | 86.4 | 78.2 | 100 | 100 |

FIG. 5 shows the sequence alignment of the upstream-promoter regions of the *Z. mays* c.v. B104 promoter compared to the upstream-promoter region of the *Z. mays* c.v. B73 Ubi-1 control promoter sequence. FIG. 6 shows the sequence alignment of the 5'-UTR or leader sequence of the *Z. mays* c.v. B104 promoter compared to the 5'-UTR or leader sequence of the *Z. mays* c.v. B73 Ubi-1 control promoter sequence. FIG. 7 shows the sequence alignment of the intronic regions of the *Z. mays* c.v. B104 promoter compared to the intronic sequence of the *Z. mays* c.v. B73 Ubi-1 control promoter sequence.

The promoter elements obtained from *Z. mays* c.v. B104 showed 85.7% overall sequence identity (Table 2) to the *Z. mays* c.v. B73 Ubi-1 sequence. Characterization of the novel promoter sequence from *Z. mays* c.v. B104 confirmed that most of the promoter regulatory elements (i.e., a TATA box or Heat Shock Element) typically found in a functional promoter, were also highly conserved within the core promoter regions of the *Z. mays* c.v. B104 promoter (Table 2). For example, FIG. 5 shows a highly conserved TATA box (base pairs 869-876 shown in italics and underlined) that was identified and found to be located approximately 50 bp 5' upstream of the TSS in the upstream-promoter region of the novel *Z. mays* c.v. B104 Ubi-1 promoter. Similarly, FIG. 5 shows two overlapping Heat Shock Element (HSE) sequences (base pairs 457-481 shown as underlined and 482-500 shown in double underlined, respectively) were conserved in the novel *Z. mays* c.v. B104 Ubi-1 promoter analyzed in this study and were located approximately 200 bp 5' upstream of the TSS.

While only small levels of variation were observed in the 5'-UTR or leader sequence of the novel *Z. mays* c.v. B104 Ubi-1 promoter as compared to the *Z. mays* c.v. B73 Ubi-1 control sequence (FIG. 6), areas of lower sequence conservation in the upstream-promoter region (FIG. 5) and intron region (FIG. 7) were also identified. In fact, most of the sequence variation in the *Z. mays* c.v. B104 promoter was specifically contributed by the intron sequence, which showed only 78.2% sequence similarity to the *Z. mays* c.v. B73 Ubi-1 intron (FIG. 7, Table 2). In particular, a 310 bp run of polynucleotides located at the 5' end of the *Z. mays* c.v. B104 intron was the most diverse (base pairs 30-340), while the 3' end of the intron was found to be fairly conserved (FIG. 7). Contrarily, the upstream-promoter and 5'-UTR regions of the *Z. mays* c.v. B104 promoter were relatively conserved (FIGS. 5 and 6), having 93.4% and 96.4% sequence identity to the *Z. mays* c.v. B73 Ubi-1 promoter, respectively (Table 2).

In addition, further regulatory motifs exist in the *Z. mays* Ubi-1 upstream-promoter region that extends 100-200 bp 5' upstream of the TSS. These motifs bind transcription factors that interact with the transcriptional initiation complex and facilitate its assembly, improve its stability, or increase the efficiency of promoter escape once the transcriptional machinery sets off (PEREMARTI et al. 2010). Thus, deletions, substitutions, and mismatches within this regulatory region could potentially affect both promoter strength and specificity.

Example 3

Vector Construction using the New Promoters for Gene Expression

Unless otherwise indicated, molecular biological and biochemical manipulations described in this and subsequent Examples were performed by standard methodologies as disclosed in, for example, Ausubel et al. (1995), and Sambrook et al. (1989), and updates thereof. The constructs used in the experiments are described in greater detail below (Table 3).

The Z. mays promoters comprising the upstream-promoter, 5'-UTR, and intronic regions, as previously described, were extracted from the Ubi-1 gene of the Z. mays 3'-UTR, was constructed. Transformation or expression vectors for *Agrobacterium*-mediated maize embryo transformation were constructed through the use of standard cloning methods and Gateway® recombination reactions employing a standard destination binary vector, pDAB101917, and the entry vectors comprising the gene expression cassettes, as described above.

The binary destination vector, pDAB101917, comprised an herbicide tolerance gene, phosphinothricin acetyltransferase (PAT; Wehrmann et al., 1996, Nature Biotechnology 14:1274-1278). In the pDAB101917 vector, PAT gene expression was under the control of a Z. mays Ubi-1 promoter, 5'-UTR, and intron. The pDAB101917 vector also comprised a 3'-UTR region from the Z. mays lipase gene (ZmLip; U.S. Pat. No. 7,179,902). The ZmLip 3'-UTR was used to terminate transcription of the PAT mRNA. The Gateway® recombination reaction enabled the insertion of each entry vector comprising the gene expression cassette (i.e., a Z. mays c.v. B104 or Z. mays c.v. B73 Ubi-1 promoter, the PhiYFP gene, and the ZmPer5 3'-UTR) into the pDAB101917 destination binary vector. The entry vectors were inserted into the pDAB101917 destination vector between T-DNA borders A and B, and upstream of the PAT expression cassette.

TABLE 3

Binary Gene Expression Vector Construction

| Binary Vector Construct | Entry Vector Construct | | | Destination Vector Construct | | | |
|---|---|---|---|---|---|---|---|
| | Promoter | Transgene | 3'-UTR | Promoter | Reporter Gene | 3'-UTR | FIG. |
| pDAB105748 | Z. mays c.v. B73 Ubi-1 | PhiYFP | ZmPer5 | Z. mays Ubi-1 | PAT | ZmLip | 8 |
| pDAB105745 | Z. mays c.v. B104 Ubi-1 | PhiYFP | ZmPer5 | Z. mays Ubi-1 | PAT | ZmLip | 9 | species and the PCR amplicons were gel purified using QIAquick Gel Extraction Kit® (Qiagen Carlsbad, Calif.). The promoter polynucleotide sequence was then cloned into a Gateway Entry Vector® (Invitrogen) using standard cloning techniques known in the art. The resulting Gateway Entry Vector® comprising the Ubi-1 promoter sequence for Z. mays c.v. B104 was confirmed via restriction digest and sequencing. A control entry vector comprising the Z. mays c.v. B73 Ubi-1 promoter sequence was also cloned into a gateway entry vector using standard cloning techniques in the art.

In addition to the Ubi-1 promoter sequences, the entry vector also comprised the yellow fluorescent protein reporter gene from the *Phialidium* species (PhiYFP; Shagin, D. A., (2004) Mol Biol Evol. 21;841-50) with an ST-LS1 intron incorporated into the sequence (Vancanneyt, G., (1990) Mol Gen Genet. 220;245-50) and the 3'-UTR region of the Zea mays Peroxidase 5 gene (ZmPer5; U.S. Pat. No. 6,699,984). Vector maps showing the cloned entry vectors comprising each of the promoter sequences are provided. Construct pDAB105742 corresponds to the control entry vector comprising the Z. mays c.v. B73 Ubi-1 promoter sequence. Construct pDAB105739 corresponds to the entry vector comprising Z. mays Ubi-1 B104 promoter sequence. Thus, entry vectors comprising gene expression cassettes comprising a Z. mays Ubi-1 promoter, the PhiYFP gene, and the ZmPer5 3'-UTR were established.

Figure 8:
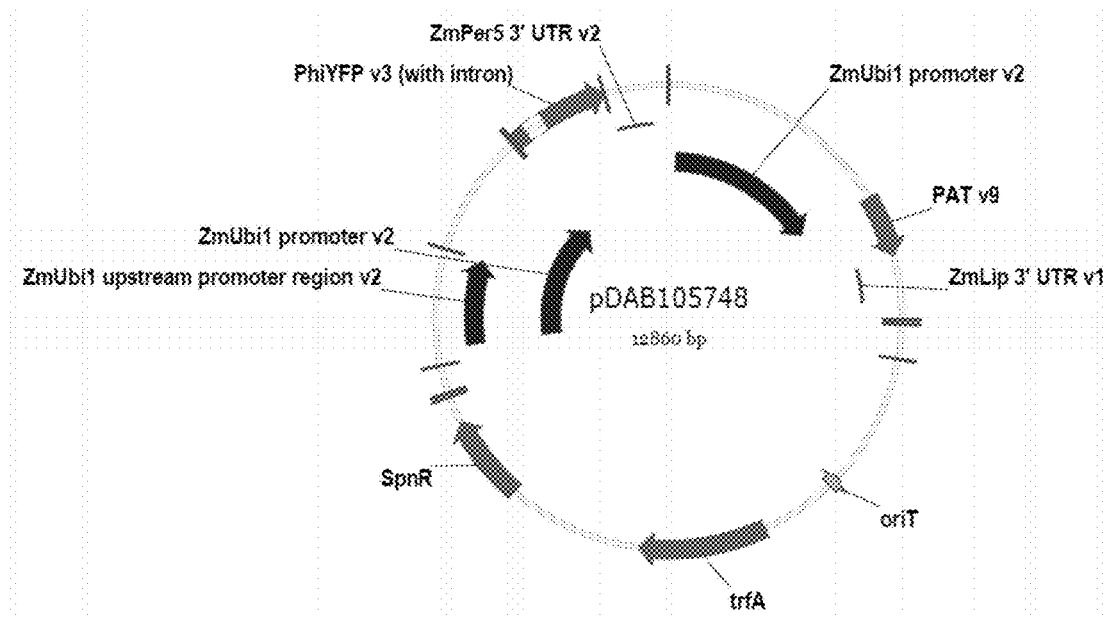
FIG. 8 shows a vector map of binary expression construct, pDAB105748, comprising the control entry vector, pDAB105742 (*Z. mays* c.v. B73), inserted into destination vector, pDAB10197.
Figure 9:
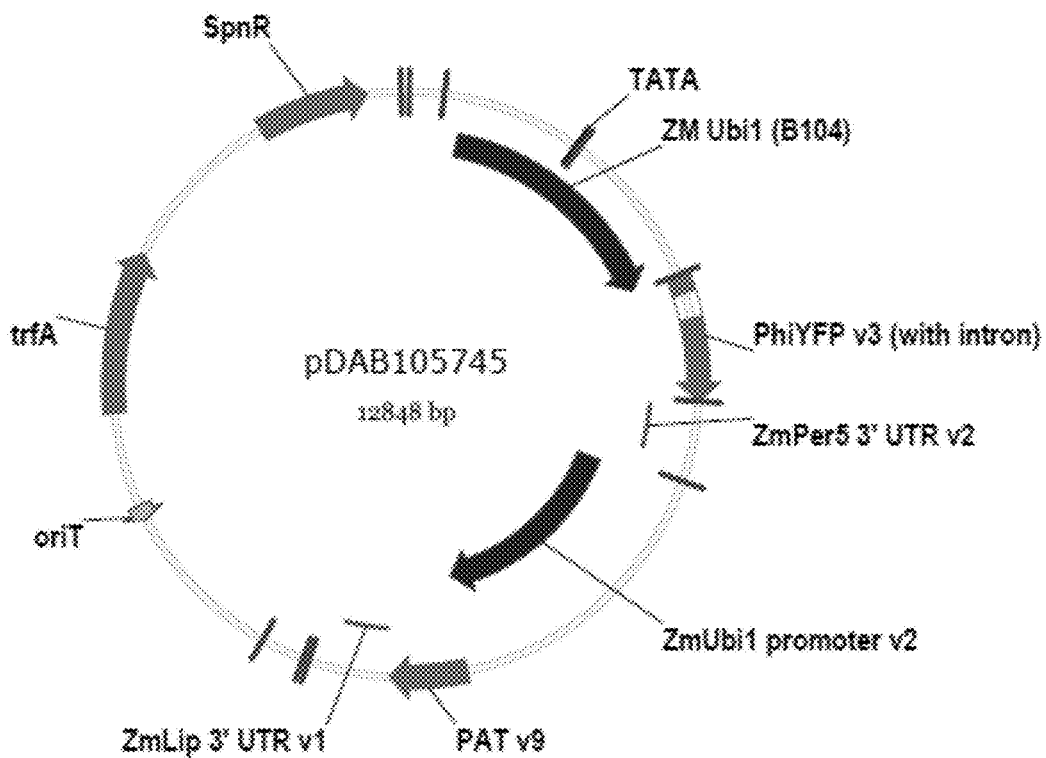
FIG. 9 shows a vector map of binary expression construct, pDAB105745, comprising the entry vector, pDAB105739 (*Z. mays* c.v. B104), inserted into destination vector, pDAB10197.

As described in Table 3, a binary expression vector construct, comprising the PhiYFP reporter gene driven by the new promoter sequence and terminated by the ZmPer5 Vector maps showing the binary expression construct, pDAB101917, with the gene expression cassettes comprised of a Z. mays Ubi-1 promoter, the PhiYFP gene, and the ZmPer5 3'-UTR incorporated, are provided. Control construct, pDAB105748, corresponds to the gene expression cassette comprising the Z. mays c.v. B73 Ubi-1 promoter (FIG. 8). In addition, construct pDAB105745 corresponds to the gene expression cassette comprising Z. mays c.v. B104 Ubi-1 promoter sequence (FIG. 9).

Example 4

Plant Transformation

Binary vector constructs, pDAB105748 (Z. mays c.v. B73) and pDAB105745 (Z. mays c.v. B104), were each transformed into the Agrobacterium tumefaciens strain, EHA101, using standard transformation techniques known in the art. Bacterial colonies were isolated and binary plasmid DNA was extracted, purified, and confirmed via restriction enzyme digestion.

Transformation of corn plants was performed according to the protocol described in Vega et al., 2008, Plant Cell Rep 27:297-305 which employed Agrobacterium-mediated transformation and the phosphinothricin acetyltransferase gene (PAT; Wehrmann et al., 1996, Nature Biotechnology 14:1274-1278) as a selectable plant marker. Agrobacterium tumefaciens cultures comprising the binary vector constructs (described above) were used to transform Z. mays c.v. Hi-II plants and produce first round, $T_0$, transgenic corn events (Table 4). The immature zygotic embryos were produced, prepared, and harvested 2.5 months after transformation.

Transformation results for the individual gene expression constructs are further described in Table 4. The total number of embryos produced, the total number of transgenic events observed at the callus stage and in the total plant, as well as the percentage of overall transformation efficiency are disclosed. Overall transformation efficiency of the binary expression constructs is lower than previously reported (Vega et al., 2008) due to poor embryo vigor in many experiments

TABLE 4

First Round, $T_0$, Corn Transformation Results

| Binary Vector Construct | Total # Embryos | Number of Callus | Number of Transgenic Events | Efficiency (%) |
|---|---|---|---|---|
| pDAB105748 | 545 | 221 | 33 | 6.1 |
| pDAB105745 | 454 | 227 | 25 | 5.5 |

Example 5

Transgene Copy Number Analysis

Stable integration of the PhiYFP transgene within the genome of the transgenic *Z. mays* plants was confirmed via a hydrolysis probe assay. Stably-transformed transgenic *Z. mays* plantlets that developed from the callus were obtained and analyzed to identify events that contained a low copy number (i.e., 1-2 copies) of full-length T-strand inserts.

The Roche Light Cycler 480™ system was used to determine the transgene copy number according to manufacturer's instructions. The method utilized a biplexed TaqMan® PCR reaction that employed oligonucleotides specific to the PhiYFP gene and to the endogenous reference gene, *Z. mays* Invertase (ZmInv; Genbank Accession No: U16123.1), in a single assay. Copy number and zygosity were determined by measuring the intensity of PhiYFP-specific fluorescence, relative to the ZmInv-specific fluorescence, as compared to known copy number standards.

A PhiYFP gene-specific DNA fragment was amplified with one TaqMan® primer/probe set containing a probe labeled with FAM™ fluorescent dye, and ZmInv was amplified with a second TaqMan® primer/probe set containing a probe labeled with HEX™ fluorescence (Table 5). Primers and probes for copy number analysis were commercially synthesized by Integrated DNA Technologies (Coralville, Iowa). The FAM™ fluorescent moiety was excited at an optical density of 465/510 nm, and the HEX™ fluorescent moiety was excited at an optical density of 533/580 nm.

PCR reactions were prepared in a final 10 µl reaction volume using reagents, as described in Table 6. Gene-specific DNA fragments were amplified according to the thermocycling conditions set forth in Table 7. Copy number and zygosity of the samples were determined by measuring the relative intensity of fluorescence specific for the reporter gene, PhiYFP, to fluorescence specific for the reference gene, ZmInv, as compared to known copy number standards.

Copy Number standards were created by diluting the vector, pDAB108706, into *Z. mays* c.v. B104 genomic DNA (gDNA) to obtain standards with a known ratio of pDAB108706:gDNA. For example, samples having one, two, and four copies of vector DNA per one copy of the *Z. mays* c.v. B104 gDNA were prepared. One and two copy dilutions of the pDAB108706 mixed with the *Z. mays* c.v. B104 gDNA standard were validated against a control *Z. mays* event that was known to be hemizygous, and a control *Z. mays* event that was known to be homozygous (i.e., *Z. mays* event 278; see PCT International Patent Publication No. WO 2011/022469 A2).

A TaqMan® biplexed PCR amplification assay utilizing oligonucleotides specific to the PAT gene and the endogenous ZmInv reference gene, respectively, was performed. PCR amplification to detect a gene-specific DNA fragment for PAT with one TaqMan® primer set and a probe labeled with FAM™ fluorescent dye was employed (Table 5). A second primer set and a probe labeled with HEX™ fluorescent dye was also used to amplify and detect the ZmInv endogenous reference/control gene (Table 5). The PAT TaqMan® reaction mixture was prepared as set forth in Table 6 and the specific fragments were amplified according to the conditions set forth in Table 7.

Results from the transgene copy number analysis of transgenic plants obtained via transformation with different promoter constructs are shown in Table 8. Only plants with 1-2 copies of the PhiYFP transgene were transferred to the greenhouse and grown for further expression analyses.

TABLE 5

Primers and Probes for Copy Number Assays

| Gene | Primer/Probe | Nucleotide Sequence | SEQ ID No: |
|---|---|---|---|
| PhiYFP | Forward Primer | CGTGTTGGGAAAGAACTTGGA | 11 |
|  | Reverse Primer | CCGTGGTTGGCTTGGTCT | 12 |
|  | Probe (Fluorescent Label/Sequence) | 5'FAM/CACTCCCCACTGCCT | 13 |
| ZmInv Control | Forward Primer | TGGCGGACGACGACTTGT | 14 |
|  | Reverse Primer | AAAGTTTGGAGGCTGCCGT | 15 |
|  | Probe (Fluorescent Label/Sequence) | 5'HEX/CGAGCAGACCGCCGTGTACTT | 16 |
| PAT | Forward Primer | ACAAGAGTGGATTGATGATCTAGAGAGGT | 17 |
|  | Reverse Primer | CTTTGATGCCTATGTGACACGTAAACAGT | 18 |
|  | Probe (Fluorescent Label/Sequence) | 5'FAM/GGTGTTGTGGCTGGTATTGCTTACGCTGG | 19 |

TABLE 6

Taqman ® Copy Number PCR Reaction Reagents

| Reagent | Working Concentration | Volume (μl) | Final Concentration |
|---|---|---|---|
| Water | — | 0.5 | — |
| Roche LightCycler Master Mix | 2X | 5 | 1X |
| PhiYFP Forward Primer | 10 μM | 0.4 | 400 nM |
| PhiYFP Reverse Primer | 10 μM | 0.4 | 400 nM |
| PhiYFP Probe-FAM labeled | 5 μM | 0.4 | 200 nM |
| ZmInv Forward Primer | 10 μM | 0.4 | 400 nM |
| ZmInv Reverse Primer | 10 μM | 0.4 | 400 nM |
| ZmInv Probe-HEX labeled | 5 μM | 0.4 | 200 nM |
| Polyvinylpyrrolidone (PVP) | 10% | 0.1 | 0.10% |
| Genomic DNA Template | ~5 ng/μl | 2 | 10 ng/μl |

TABLE 7

Thermocycling Conditions for Copy Number PCR Amplification

| PCR Step | Temperature (° C.) | Time | Number of Cycles |
|---|---|---|---|
| 1 | 95 | 10 minutes | 1 |
| 2 | 95 | 10 seconds | 40 |
|   | 58 | 35 seconds |   |
|   | 72 | 1 second |   |
| 3 | 40 | 10 seconds | 1 |

TABLE 8

Transgene Copy Number Analysis of Transgenic Plants

| Construct | Events Analyzed | Simple (1-2 copies) | Complex (>2 copies) |
|---|---|---|---|
| 105748 | 21 | 15 | 6 |
| 105745 | 11 | 9 | 2 |

Example 6

ELISA Quantification of PhiYFP and PAT Proteins

Plants were sampled at V4-5 stage of development using a leaf ELISA assays. Samples were collected in 96-well collection tube plates and 4 leaf disks (paper hole punch size) were taken for each sample. Two 4.5 mm BBs (Daisy corporation, Roger, Ark.) and 200 μL extraction buffer [1× PBS supplemented with 0.05% Tween®-20 and 0.05% BSA (Millipore Probumin®, EMD Millipore Corp., Billerica, Mass.)] were added to each tube. Additional 200 μL of extraction buffer was added to each tube followed by inversion to mix. Plates were spun for 5 minutes at 3000 rpm. Supernatant was transferred to corresponding wells in a deep well 96 stored on ice. The Nunc® 96-well Maxi-Sorp Plates (Thermo Fisher Scientific Inc., Rockford, Ill.) were used for ELISA. Plates were coated with mouse monoclonal anti-YFP capture antibody (OriGene Technologies Inc., Rockville, Md.). The antibody was diluted in PBS (1 μg/mL) and 150 μL of diluted PBS was added per well. The plates were incubated overnight at 4° C. The overnight plates were kept at room temperature for 20-30 minutes before washing 4× with 350 μL of wash buffer [lx PBS supplemented with 0.05% Tween®-20 (Sigma-Aldrich, St. Louis, Mo.)]. Plates were blocked with 200 μL per well of blocking buffer [lx PBS supplemented with 0.05% Tween®-20 plus 0.5% BSA (Millipore Probumin®)] for a minimum of 1 hr at +37° C. followed by 4× washing with 350 μL of wash buffer (Tomtec QuadraWash™ 2, Tomtec, Inc., Hamden, Conn.).

For the YFP ELISA, Evrogen recombinant Phi-YFP 1 mg/mL (Axxora LLC, Farmingdale, N.Y.) was used as a standard. A 5-parameter fit standard curve (between the 1 ng/ml and 0.125 ng/ml Standards) was used to ensure all data fall in the linear portion of the curve. 100 μL of standard or sample was added to the well. A minimum 1:4 dilution of sample in the Assay Buffer was used. Plates were incubated for 1 hr at room temperature on plate shaker (250 rpm; Titer Plate shaker) followed by 4× washing with 350 μL of wash buffer (Tomtec QuadraWash™ 2). About 100 μL of 1 μg/mL Evrogen rabbit polyclonal anti-PhiYFP primary antibody (Axxora) was added to each well. Plates were incubated for 1 hr at room temperature on a plate shaker at 250 rpm followed by 4× washing with 350 μL of wash buffer (Tomtec QuadraWash™ 2). Next, 100 μL of anti-rabbit IgG HRP secondary antibody (Thermo Scientific) diluted 1:5000 in Blocking/Assay buffer, which PAT proteins were quantified using kit from Envirologix (Portland, Me.). The ELISAs were performed using multiple dilutions of plant extracts and the reagents and instructions essentially as provided by the suppliers.

Example 7

Stable Plant Expression of Transgene Operably-Linked to Novel Promoters

Figure 10:
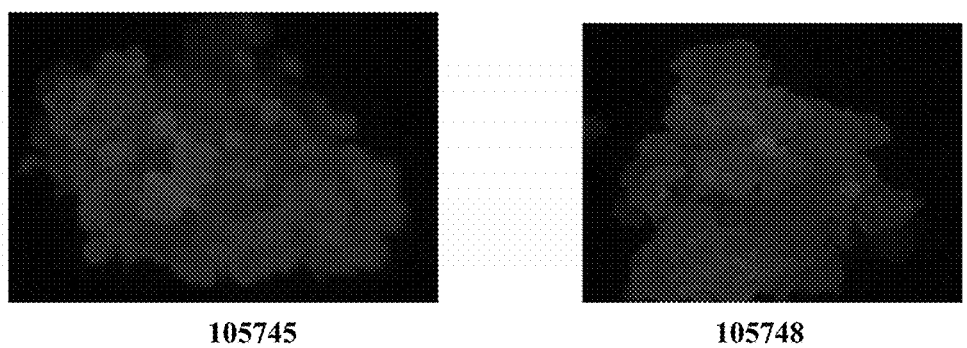
FIG. 10 shows PhiYFP gene expression in $T_o$ plant calli for binary expression constructs pDAB105748 (*Z. mays* c.v. B73) and pDAB105745 (*Z. mays* c.v. B104).

Protein expression was observed in transgenic plant tissues. For example, PhiYFP expression was observed in calli of $T_0$ plants that were stably transformed by co-cultivation with *Agrobacterium*. The transgenic plants were grown from *Z. mays* embryos transformed using the binary vector constructs comprising the novel promoter, pDAB105745 (*Z. mays* c.v. B104, FIG. 9) and the control promoter, pDAB105748 (*Z. mays* c.v. B73, FIG. 8). The plant calli were observed under a stereomicroscope (Leica Microsystems, Buffalo Grove, Ill.) using an YFP filter and a 500 nm light source. Representative examples of the stable expression of PhiYFP observed in the callus tissue of the transgenic $T_0$ maize plants comprising pDAB105745 as compared to the control, pDAB105748, are shown in FIG. 10. The data confirms that the novel promoter comprising pDAB105745 (*Z. mays* c.v. B104), as described herein, is able to drive robust expression of the PhiYFP gene in callus tissue of $T_0$ transgenic plants.

As described in Table 8, whole plants that contained a low copy number (i.e., 1-2 copies) of the PhiYFP transgene were grown in a greenhouse. In general, about five (5) to about ten (10) events per construct and about five (5) plants per event were used for $T_1$ expression analysis. The ELISA data revealed consistent expression of the PhiYFP protein in the leaves of $T_1$ corn plants using vector constructs comprising the novel promoter, pDAB105745 (*Z. mays* c.v. B104), compared to the control construct, pDAB105748 (*Z. mays* c.v. B73).

A mean PhiYFP protein expression of approximately 347 ng/mg (+/−22.9 ng/mg) of PhiYFP was observed for the $T_1$ plants comprising the novel promoter construct, pDAB105745 (*Z. mays* c.v. B104, FIG. 9), as compared to approximately 285.3 ng/mg (+/−22.7 ng/mg) of PhiYFP protein produced by the control plant comprising the control construct, pDAB105748 (*Z. mays* c.v. B73, FIG. 8). These results confirm that the novel promoter from *Z. mays* c.v. B104, as disclosed herein, was useful in producing transgenic traits at high levels of protein production.

In addition, the mean PAT expression for all T₁ plants comprising pDAB105745 (*Z. mays* c.v. B104) was approximately 93.7 ng/mg (+/−7.4) as compared to approximately 105.8 ng/mg (+/−7.4 ng/mg) of PAT protein produced by the control plant comprising pDAB105748 from the *Z. mays* c.v. B73 promoter. Overall, the expression of PAT protein for all maize plants was significantly lower than the expression observed for the PhiYFP gene in maize plants.

Figure 11:
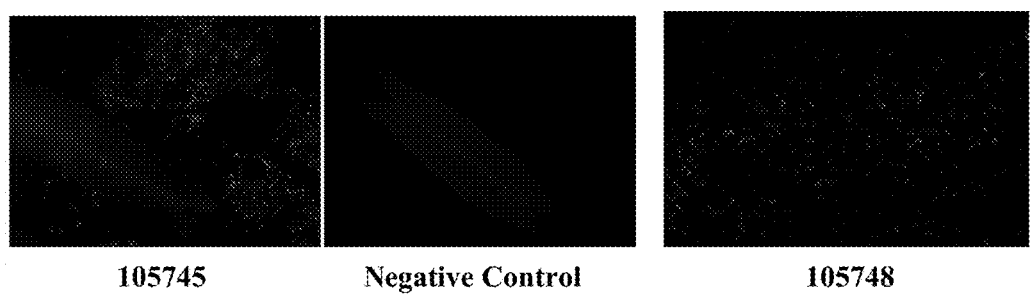
FIG. 11 shows PhiYFP gene expression in $T_1$ plant pollen for binary expression constructs pDAB105748 (*Z. mays* c.v. B73), pDAB105745 (*Z. mays* c.v. B104), and a negative control.

PhiYFP protein expression was also measured in pollen derived from the tassels of selected T₁ transgenic plants representing each of the novel promoter constructs described herein. As shown in FIG. 11, image analysis of the transgenic pollen confirms that the novel promoter comprising pDAB105745 (*Z. mays* c.v. B104), as described in this application, drives high expression of PhiYFP protein in pollen.

What is claimed is:

1. A construct comprising a promoter sequence comprising SEQ ID NO: 2 operably linked to a heterologous nucleic acid sequence.

2. A construct comprising the complement to the promoter sequence of SEQ ID NO: 2 operably linked to a heterologous nucleic acid sequence.

3. The construct of claim 1, wherein the operably linked heterologous nucleic acid sequence encodes a heterologous polypeptide.

4. A gene expression cassette comprising the construct of claim 1 operably linked to a 3'-untranslated region.

5. The gene expression cassette of claim 4, wherein the operably linked heterologous nucleic acid sequence encodes a polypeptide that confers a trait selected from the group consisting of insecticidal resistance, herbicide tolerance, nitrogen use efficiency, water use efficiency, nutritional quality, DNA binding, and selectable marker.

6. A recombinant vector comprising the gene expression cassette of claim 4.

7. The recombinant vector of claim 6, wherein the vector is selected from the group consisting of a plasmid vector, a cosmid vector, and a BAC vector.

8. A transgenic cell comprising the construct of claim 1.

9. The transgenic cell of claim 8, wherein the transgenic cell is a transgenic plant cell.

10. A transgenic plant comprising the transgenic plant cell of claim 9.

11. A transgenic seed comprising the construct of claim 1.

12. The transgenic plant of claim 10, wherein the transgenic plant is a monocotyledonous or dicotyledonous transgenic plant.

13. A transgenic plant tissue comprising the construct of claim 1.

14. The transgenic plant tissue of claim 13, wherein the transgenic plant tissue is selected from the group consisting of a root, a shoot, a stem, and a pollen tissue.

15. The transgenic plant of claim 12, wherein the transgenic plant is a monocotyledonous plant.

16. The transgenic plant of claim 15, wherein the monocotyledonous plant is selected from the group consisting of a maize plant, a wheat plant, and a rice plant.

17. The construct of claim 1, wherein the operably linked heterologous nucleic acid sequence encodes a polypeptide selected from the group consisting of the Yellow Fluorescent Protein from the *Phialidium* species (PhiYFP) and phosphinothricin-N-acetyl-transferase (PAT).

* * * * *